US010117719B2

(12) United States Patent
Cerda et al.

(10) Patent No.: US 10,117,719 B2
(45) Date of Patent: Nov. 6, 2018

(54) SYSTEM, METHOD AND DEVICE FOR A MEDICAL SURGERY TRAY

(71) Applicants: John Paul Cerda, Ripon, CA (US); Mark Lowenstein, Sandy, OR (US); Julio Armando Cerda-Gutierrez, Bell Gardens, CA (US)

(72) Inventors: John Paul Cerda, Ripon, CA (US); Mark Lowenstein, Sandy, OR (US); Julio Armando Cerda-Gutierrez, Bell Gardens, CA (US)

( * ) Notice: Subject to any disclaimer, the term of this patent is extended or adjusted under 35 U.S.C. 154(b) by 0 days.

(21) Appl. No.: 15/367,468

(22) Filed: Dec. 2, 2016

(65) Prior Publication Data

US 2017/0156811 A1 Jun. 8, 2017

Related U.S. Application Data

(60) Provisional application No. 62/263,022, filed on Dec. 4, 2015.

(51) Int. Cl.
*B65D 83/10* (2006.01)
*A61B 50/33* (2016.01)
(Continued)

(52) U.S. Cl.
CPC .............. *A61B 50/33* (2016.02); *A61B 46/00* (2016.02); *A61B 46/10* (2016.02); *B65B 55/04* (2013.01); *B65B 55/12* (2013.01); *A61B 90/94* (2016.02); *A61B 2050/3008* (2016.02); *A61B 2050/3009* (2016.02)

(58) Field of Classification Search
CPC ......... A61B 50/33; A61B 46/00; A61B 46/10; A61B 46/23; A61B 50/362; A61B 50/3007; B65B 55/04; B65B 55/12; B65D 21/0202; B65D 21/02
USPC ....... 206/370, 363, 223, 558, 438, 504, 364, 206/471; 220/23.2, 23.6, 23.83, 23.86, 220/4.22, 4.21, 4.24
See application file for complete search history.

(56) References Cited

U.S. PATENT DOCUMENTS

| | | | | |
|---|---|---|---|---|
| 1,787,387 A | * | 12/1930 | Marz ........................ | B42F 7/10 206/449 |
| 2,505,510 A | * | 4/1950 | Vermillion ............. | A47G 21/14 206/372 |

(Continued)

*Primary Examiner* — Rafael Ortiz
(74) *Attorney, Agent, or Firm* — John P. Costello; Costello Law Corp.

(57) ABSTRACT

A method and system for organizing surgical instruments and supplies in an operating room in preparation for surgery using a system having two tray devices. Each tray includes at least one flat work surface disposed in a first reference plane; an edge feature surrounding the at least one flat work surface, the edge surface standing proud at a predetermined first positive offset distance from the first reference plane, the edge feature comprising at least a work-surface-side wall intersecting the at least one flat work surface at substantially about 90-degrees at a top surface coupled to the work-surface-side wall, wherein the top surface disposes generally parallel to the first reference plane and is further defining the first positive offset distance measured from the reference plane; and at least one recessed compartment comprising a bottom surface disposed parallel to the first reference plane and offset therefrom at a first negative offset distance.

6 Claims, 13 Drawing Sheets

(51) Int. Cl.
   *A61B 46/00* (2016.01)
   *B65B 55/04* (2006.01)
   *B65B 55/12* (2006.01)
   *A61B 46/10* (2016.01)
   *A61B 50/30* (2016.01)
   *A61B 90/94* (2016.01)

(56) References Cited

U.S. PATENT DOCUMENTS

| | | | | |
|---|---|---|---|---|
| 4,153,160 A * | 5/1979 | Leigh | ............ | B65D 1/36 206/370 |
| 4,643,303 A * | 2/1987 | Arp | ............ | A61L 2/26 206/370 |
| 4,899,877 A * | 2/1990 | Kiernan | ............ | B65D 75/245 206/349 |
| 5,129,516 A * | 7/1992 | Theros | ............ | B65D 75/225 206/389 |
| 5,170,804 A * | 12/1992 | Glassman | ............ | A61B 50/10 128/849 |
| 5,447,232 A * | 9/1995 | Chow | ............ | B65D 75/245 206/372 |
| 5,451,380 A * | 9/1995 | Zinnanti | ............ | A61L 2/26 206/370 |
| 6,426,041 B1 * | 7/2002 | Smith | ............ | A61L 2/26 206/223 |
| 7,066,328 B2 | 6/2006 | Pulsifer | | |
| 7,565,972 B2 | 7/2009 | Steppe | | |
| 8,910,789 B2 * | 12/2014 | Lewis | ............ | B65D 43/162 206/470 |
| 2005/0252812 A1 * | 11/2005 | Lewis | ............ | B65D 75/225 206/461 |
| 2008/0308698 A1 * | 12/2008 | Steppe | ............ | A61L 2/26 248/274.1 |
| 2011/0155599 A1 * | 6/2011 | Yakel | ............ | A61B 19/0271 206/365 |
| 2012/0234781 A1 * | 9/2012 | Cogliano | ............ | B25H 3/026 211/85.13 |
| 2013/0200023 A1 * | 8/2013 | Brotzman | ............ | A61B 19/0256 211/85.13 |
| 2013/0334083 A1 * | 12/2013 | Bugnard | ............ | A61B 19/0271 206/370 |
| 2014/0014544 A1 * | 1/2014 | Bugnard | ............ | A61C 19/02 206/369 |
| 2014/0138269 A1 * | 5/2014 | Ghosh | ............ | A61B 19/0271 206/370 |
| 2014/0138270 A1 * | 5/2014 | Ghosh | ............ | A61B 50/13 206/370 |
| 2015/0060462 A1 * | 3/2015 | Colbert | ............ | A61M 5/002 220/553 |

* cited by examiner

SYSTEM, METHOD AND DEVICE FOR A MEDICAL SURGERY TRAY

PRIORITY CLAIM

The present application claims benefit under 35 USC Section 119(e) of U.S. Provisional Patent Application Ser. No. 62/263,022 filed on 4 Dec. 2015 titled "System, Method, and Device for a Medical Surgery Tray" by a common inventor: The present application is based on and claims priority from this application, the disclosure of which is hereby expressly incorporated herein by reference.

FIELD OF THE INVENTION

This invention relates generally to surgical instruments and, more specifically, to a standardized procedural methodology utilizing trays for transporting sterile surgical instruments to an operating room and presenting the instruments in a standardized configuration and order, ready-to-use and appropriate for nearly all types of surgery.

BACKGROUND

Storage and sterilization systems for veterinary and human dental and medical instruments are known in the art. Many devices include features to stack and space. In the art of medical surgical instruments, storage trays for sterilization and storage of instruments are common. However, such systems have limitations. For example, one type of tray, although well adapted for use in a first surgical procedure, is ill suited for a second type of surgical procedure. A general instrument tray, commonly used in many operating room procedures, is not suitably versatile to adapt for use as operating room procedures change, are modified, or are replaced with new procedures.

The term "general instrument tray" refers to a set of devices commonly used in surgery and includes ringed instruments such as snaps, clamps, Kellys, Ailises, Babcocks, Kochers, needle holders, sponge sticks and scissors, among other rigid instruments. Prior to use, a general instrument tray is sterilized and packaged at a location remote from a surgery suite. Before a specific surgery or procedure, the requisite sterilized instrument tray(s) are sent to the surgery suite, which is being prepared for that specific procedure. In the operating room a back table is lined with sterile drapes. Then, sterile supplies are removed from their outer packaging and placed on this back table. One surgical nurse does a surgical scrub, puts on a sterile gown and gloves and rearranges the multiple sterile supplies needed for the given procedure—placing them in an arrangement and order—not governed by specific instructions, not standardized, but rather based on that person's experience and preference, which is determined in part on the nature of the surgical procedure and the anticipated sequence of use, probable outcomes, potential error-mitigation efforts, and other criteria.

During this preparation, the ringed instruments are removed from sterile buckets and unstrung from each of two long-armed "stringers." The buckets include other instruments that are not strung on the stringers, but are, rather, left loose in the bottom of the bucket. These instruments, too, need to be arranged for later use and are placed on the back table. Once all the supplies and instruments are arranged a required complete count of all the instruments and supplies is made.

The lack of standardization causes delays in both the initial preparation of the instruments and, more critically, during surgery, especially when a scrub nurse is commonly relieved during a procedure. The replacement scrub nurse, who did not arrange the instruments, does not have implicit knowledge of the location of each instrument or supply. This is a known limitation of the aforementioned method.

Currently used instrument trays contain grooves or recesses, which are designed for specific, individual instruments. While many of these known trays include additional mechanisms or features configured to hold specific individual instruments in a preferred orientation, they are not optimized to hold a large quantity of varying instruments in an "operation ready" position. Other known trays increase adaptability by providing removable section dividers combined with fixed section dividers. However, this is disadvantageous as the removable dividers must be accounted for and can be dislodged during use. This adds risk by potentially becoming lost inside the patient during surgery, or simply dislodged causing one or more instruments to be disrupted while on the tray, thus delaying the surgical process, for example.

One known device in the art is a multipurpose surgical instrument tray disclosed by Smith in U.S. Pat. No. 6,426,041, and issued on 2002 Jul. 2. One significant limitation of the Smith device, as illustrated best in FIG. 3 of Smith, is that both a portion of the ring-end of a surgical instrument and the "sharp" end of the same instrument rests above, or stands proud, in relation to a first flat top surface of the tray. This enables users to be cut or punctured by the sharp end of the instrument, which is very undesirable. It also leaves the sensitive tips of the medical instruments exposed and subject to damage and degradation, thus requiring replacement often.

Other known devices and techniques include protective tip covers designed to protect the patient and staff from sharps injury with a certain degree of success. However, the success is limited as frequently these sharps protective tips must be carefully examined prior to use and the sharp instrument frequently cuts through the protective tip and wrapper or package. This methodology is limited in that it relies upon visual inspection by a trained, naked eye, and as such is highly variable and prone to human error. Furthermore, presuming all sharp tips are protected, well-inspected, and delivered to the sterile field, and then the protected instruments are properly placed on the Mayo stand and for back table, the removed sharps protective tips are not tracked once they are removed from the instrument. Thus presents a major disadvantage, as it is known that these discarded protective tips may manage to find a way into the patient; this presents as a foreign object with ensuing poor patient outcomes and resultant adverse legal implications.

Other known art includes U.S. Pat. No. 7,565,972, issued on 2009 Jul. 28, titled "Medical Equipment Tray System" to Steppe. This medical equipment tray system includes three parts: a platform portion, a foldable liner, and a hand-piece cradle. Another known reference includes a "Grooved Angled Tray for Ring-Handled Surgical Instrument," described in U.S. Pat. No. 7,066,328, issued on 2006 Jun. 72 to Pulsifer.

To date there is no known or proven methodology that adequately protects the patient and the users from sharps injury, while at the same time securing and protecting the surgical instruments themselves from damage and facilitating a faster more accurate accounting of instruments and materials at all relevant times of a surgical operation. And, despite attempts in the art at improving surgical trays, there remains a need for an improved surgical tray that retains all the general/major/trauma instruments, arranges these instruments in a ready-to-use orientation, allows these instruments to be sterilized and re-sterilized ahead of use, delivered to the operating room sterile, and minimizes set up time. Further, there remains a need for a system and method that standardizes safe and efficient operating procedures. Use of the disclosed surgical instrument tray in conjunction with the surgical back table using an imprinted mapped back table drape that provides for specific designated areas for specific surgical instruments and materials commonly present and used addresses this need. Also, there is a need for a standardized tray that readily, easily, quickly, economically, and efficiently adapts for various uses.

SUMMARY OF THE INVENTION

The present invention contemplates a system and method that uses a one- or two-tiered surgical tray specific to the type of surgical procedure being performed, and a standardized back table drape having an imprinted mapped out orientation designating specific locations for a second-tier tray and other surgical materials. The primary tray, which is placed on a Mayo stand, also features a unique tray which is attached by mechanical armature to the primary tray. This allows the unique tray to be presented, retracted and manipulated in and out of the sterile field. The unique tray is equipped with recessed slotted areas specifically designed to hold, transfer, receive and secure sharps instruments between the surgical scrub nurse and the surgeon during intraoperative surgical procedures.

The trays use unique features and elements that standardize and efficiently organize instruments. The method improves the safety and efficiency of relaying the instruments during the surgical procedure. The surgical tray of the present invention can be conventionally sterilized and purposefully arranges surgical instruments in a perpendicular fashion in a space and manor similar to that used by surgical scrub nurses on their conventional Mayo stand and back tables, as well as to hold, and display with easy access, a predetermined number of surgical instruments in pre-designated locations. This serves to safe guard against commonly occurring sharps injuries to the patient and staff members of the preoperative setup, intraoperative procedure, and the post-operative re-sterilization process, in addition to preventing post-operative retained foreign objects in patients, effectively decreasing surgeon and medical malpractice liability costs. Additionally, the trays and back table drape, used in the method of set up contemplated, facilitates faster, more efficient and accurate accounting of surgical instruments and materials present in the operating room.

The tray may be sterile processed in an approved sterilization container and delivered to the operating room in a sterile manner and quickly accessed for use. The design and construction of the tray, with recessed sections of defined shapes and sizes, designed to accommodate specific instruments and retractors, enables a user to extract a given instrument from the tray in a "ready position", which may then be relayed to the surgeon with no further manipulation of the instrument.

The tray of the present invention, accordingly, is delivered to the operating room in a "ready-to-use" state, with the tray pre-populated with instruments. Each instrument is in a predetermined location on the tray, with the tray having features that retain each individual instrument in a predetermined orientation. This minimizes scrub nurse set up time, increases safety, improves efficiencies, and further helps to minimize procedural operating room count time between the scrub nurse and the circulating operating room nurse, while safely and simultaneously protecting the patient and operating room staff from commonly occurring sharps injuries during the preoperative, intraoperative and postoperative phases of the surgical procedure as well as protecting and safeguarding the surgical instruments.

The present invention further reduces preoperative set up time.

Without limitation, one aspect of the claimed invention includes a medical surgery tray for holding at least one medical instrument having a handle end and a working end. The tray is comprised of at least one substantially flat work surface disposed in a first reference plane, an edge feature surrounding the at least one substantially flat work surface that stands proud at a predetermined first positive offset distance from the first reference plane and comprises at least a work-surface-side wall intersecting the at least one substantially flat work surface at substantially 90-degrees at a top surface coupled to the work-surface-side wall, wherein the top surface disposes generally parallel to the first reference plane and further defines the first positive offset distance measured from the reference plane; and at least one recessed compartment comprising a bottom surface disposed substantially parallel to the first reference plane and offset therefrom at a first negative offset distance. The at least one recessed compartment further comprises a first support truss disposed intermediate to the reference plane and the bottom surface, the first truss comprising at least one tool-support notch and a cooperating and corresponding second support truss comprising at least one sharps-end support groove disposed at a negative offset from the reference plane and the groove further configured whereby the instrument inserted in the cooperating tool-support notch and sharps-end groove arranges the working end of the medical instrument to lie below the first reference plane.

In one embodiment, the tray further comprises a second recessed compartment separate from the first recessed compartment, the second recessed compartment comprising a circular opening in the work surface and having at least one curvilinear sidewall extender therefrom downward intersecting with a bottom-platform recessed in a negative offset from the reference plane whereby the second recess compartment configures to accept a fluids container.

Another aspect of the claimed invention encompasses a system for organizing a plurality of surgical instruments and a plurality of surgical supplies in a sterile operating room in preparation for a procedure, operation, or surgery. The system is comprised of a first tray and a second tray as described in the foregoing aspect, a linking support member adapted to couple to the first tray at a first proximal end of the linking support member and selectively attach to the second tray device at a second distal end of the linking support member whereby the linking support member is further configured to enable the second tray to rotate into and out of a field of sterilization and further configured to rotatably move from a first position over the first tray; and the linking support member further comprises an intermediate hinge disposed between the distal and proximal ends.

In one embodiment of the system the linking support member comprises a swing-arm bracket configured to couple to the work surface of the first tray, the swing-arm bracket further comprising a coupling member configured to engage a portion of the sidewall and work surface of the first tray, the coupling member further including a sleeve. A first arm member comprising a pin is disposed on a proximal end, the pin configured to slideably engage the sleeve and whereby the pin rotates in the sleeve, the first arm member further comprising a distal end having a first-hinge end. A second arm member is comprised of a cooperating second-hinge end configured to hingeably engage the first-hinge end and disposed on a proximal end of the second arm member, a distal end of the second arm member includes a post; and the second tray further comprises a post-receiving hole configured to rotatably receive the post of the second arm member, the second tray configured to be supported by the swing arm in at least one position offset from the tray. At least one work surface defines a given reference plane, at least one recessed compartment offset at a negative distance from the given reference plane configured to selectively hold at least one surgical instrument in a position whereby the working end is below the given reference plane.

In another embodiment of the system at least one surgical drape has at least one predefined area printed thereon. The surgical drape is configured to cover a back table in the operating room, with the predefined area indicating the systematic placement of at least one surgical instrument or supply.

In yet another aspect of the disclosed invention, a method for organizing a plurality of surgical instruments and a plurality of surgical supplies in a sterile operating room in preparation for a procedure, operation, or surgery, is provided. The method comprises providing or selecting the system disclosed herein; placing at least one instrument into a specific location in a first tray, conducting a pre-operative accounting of instruments by visually inspecting the tray and observing that there is a corresponding instrument in each specific location, and recording the results of the pre-operative accounting.

An embodiment of the method of further comprises conducting a preoperative, interoperative and final or closing accounting and placing counted instruments in a contamination-container and transferring the container to the sterile processing department, sterilizing one or more instruments, and sterilizing at least one of the first or second tray.

In still another aspect of the disclosed invention, a method comprises providing a plurality of trays, a first tray according to claim 1, and a second tray also according to claim 1; placing the upper tray on a Mayo stand; coupling the first tray to a second tray by using a swing arm bracket; placing the second tray outside a sterile field by rotating the bracket away from the first tray; placing the first tray and Mayo stand in the sterile field; and placing the second tray on a specifically designated location on a back table, the back table being covered by a drape having at least one specific location demarked thereon.

The present invention improves over the known art and includes many advantages, including, but not limited to:

(A) Promoting safety of patients and staff during the intra-operative process. The importance of improved safety during the intra-operative is defined annually by The Joint Council on Accreditation of Hospitals (JCAHO) an organization made up of individuals from the private medical sector to develop, maintain, and promote standards of quality care in medical facilities. In November 2015 the JCAHO website cited the need for universal protocols to increase patient safety. Failure of Hospitals to meet the JCAHO requirement may have severe penalties levied against them. According to the World Health Organization (WHO), patient safety is a fundamental principal of healthcare. The caregiving process is inherently risky and adverse events may result from problems in practice, products and procedures, or systems. Patient safety improvements demand a complex, system-wide effort that involves performance improvement, environmental safety, risk management, equipment safety, safe clinical care, and safe environmental care. WHO further defines patient safety as: "The prevention of errors and adverse effects to patients associated with health care." The present invention addresses, answers and improves upon many of the critical issues and the objectives of these national and international governing and oversight health care organizations (B) The trays of the various preferred embodiments of the present invention comply with and exceed the 2000 Federal Needle Stick and Prevention Act currently in effect and are designed for patient and staff safety to decrease sharp injuries. The sharp instruments are recessed into the tray so, for example, the scrub person may move their arm across the entire tray without a single sharps cut or stab from the sharp instruments.

(C) The disclosed trays include one or more lateral slots to accept individual instruments and to retain each instrument in a specific slot, which can be predetermined by a procedure or method of the present invention. Each slot is further recessed to ensure that the sharp end of the instrument lies below the working surface plane of the tray. This ensures that the tray complies with The 2000 Federal Needle stick Safety and Prevention Act currently in effect, by identifying and improving the cited "no hands passing of sharps, syringe needles, trocars etc.", and allows for intraoperative relay of dangerous sharp surgical instruments by incorporating the arm and accompanying sharps carrier of the present invention, thus decreasing the potential for injury to staff and patients during the relay process.

(D) The disclosed system meets and exceeds the 2000 national Occupational Safety and Health Administration (OSHA) recommendations and citations currently in effect.

(E) The disclosed system and methodology complies with the Association of Perioperative Registered Nurses, the National Operating Room Nurses Associations recommendations (AORN), and the Association of Surgical Technologists (AST) by safely and efficiently providing a standardized minimum number of instruments to the Mayo stand for perioperative procedures.

(F) The disclosed trays are part of a standardized surgical system and method used intra-operatively. This eliminates guesswork in Mayo stand and back table set up.

(G) The disclosed trays are positioned to safely and easily allow a constant running accountability of surgical instruments presented at all phases of the surgical procedure, which helps decrease retained foreign objects in patients and increase patient safety outcomes while decreasing medical malpractice claims to hospitals and surgeons.

(H) The disclosed trays, when used in the standardized method disclosed herein facilitate and promote the safe ease of relaying surgical instruments.

(I) When used according to a preferred method according to the present invention, the disclosed trays decrease medical liability to all parties concerned and incorporate a "no empty slot design" during the perioperative procedure.

(J) The disclosed trays provide a quick view of surgical instruments in an instant without further manipulation.

(K) The disclosed trays each contain a curved recessed perimeter underneath each tray that is easily adapted and stabilized to the standard Mayo tray.

(L) When used according to a preferred method, the disclosed trays reduce mental stress to the operating room personnel under stressful situations by complying with current national operating room standards of safety, and efficiency by introducing a standardized minimum number of instruments to the Mayo stand in less than a few minutes when used for emergency surgeries, routine surgeries or as a change in the surgical procedure dictates to sustain life or promote patient outcomes.

(M) The system safely decreases intraoperative set up time and break down time.

(N) The trays and system are designed to create specific and pre-designated "free work space" areas.

(O) The disclosed trays incorporate and establish a design to promote operating room technique as standardized surgical procedures on an international level.

(P) The disclosed trays allow for safety and "ease of hand-off" to the break or relief person by using a standardized configuration and by decreasing the number of displaced sharps and surgical instruments.

(Q) The disclosed trays decrease costs to surgical facilities by decreasing the number of unnecessary instruments sent into the operating room through a standardized preparation of instruments and trays.

(R) The disclosed system reduces costs to hospitals and surgical suites by providing safe, standardized set up methods and procedures and reduces downtime between surgical procedures.

(S) The system allows and promotes faster training of operating room personnel.

(T) The disclosed trays are easily adapted for use by operating room technicians, licensed nurses, and—in true emergencies—the surgeons.

(U) The disclosed tray, system, and procedures adapt well for implementation in the Military, including remote field hospitals.

(V) The standardization of surgical set up promotes positive patient and staff outcomes of each surgical procedure in various settings including, but not limited to: in-patient hospitals, out-patient surgical centers, doctor offices, and veterinary surgical settings.

(W) There are standardized trays adapted for most surgical procedures.

(X) The disclosed trays, system and method promote new higher safety standards according to the International Association of HealthCare Service Materials Management (IAHCSMM) through preparation in a standardized fashion to maintain accuracy or processing of sterilized instruments and trays.

(Y) The disclosed trays, system and method meet or exceed current safety standards and demands as defined by the World Health Organization (WHO), as well those standards mandated by local, state and federal government health agencies currently advocating and enforcing standardization in the hospital setting.

(Z) The disclosed trays, in one embodiment, are constructed using a modular component design comprising a base containment platform which is designed to rest on a Mayo stand. The interior section of each tray is divided up into four separate component sections which are attached, fashioned and joined to the base unit using attachment locking mechanisms to fasten and hold all of the components in place. This allows the end-user to exchange and replace sections of trays as needed without replacing the entire tray system. The functional design characteristics, intended use and applications remain the same, providing the same benefits as all other embodiments of the design and system.

DRAWINGS

DESCRIPTION OF THE INVENTION

Figure 1:
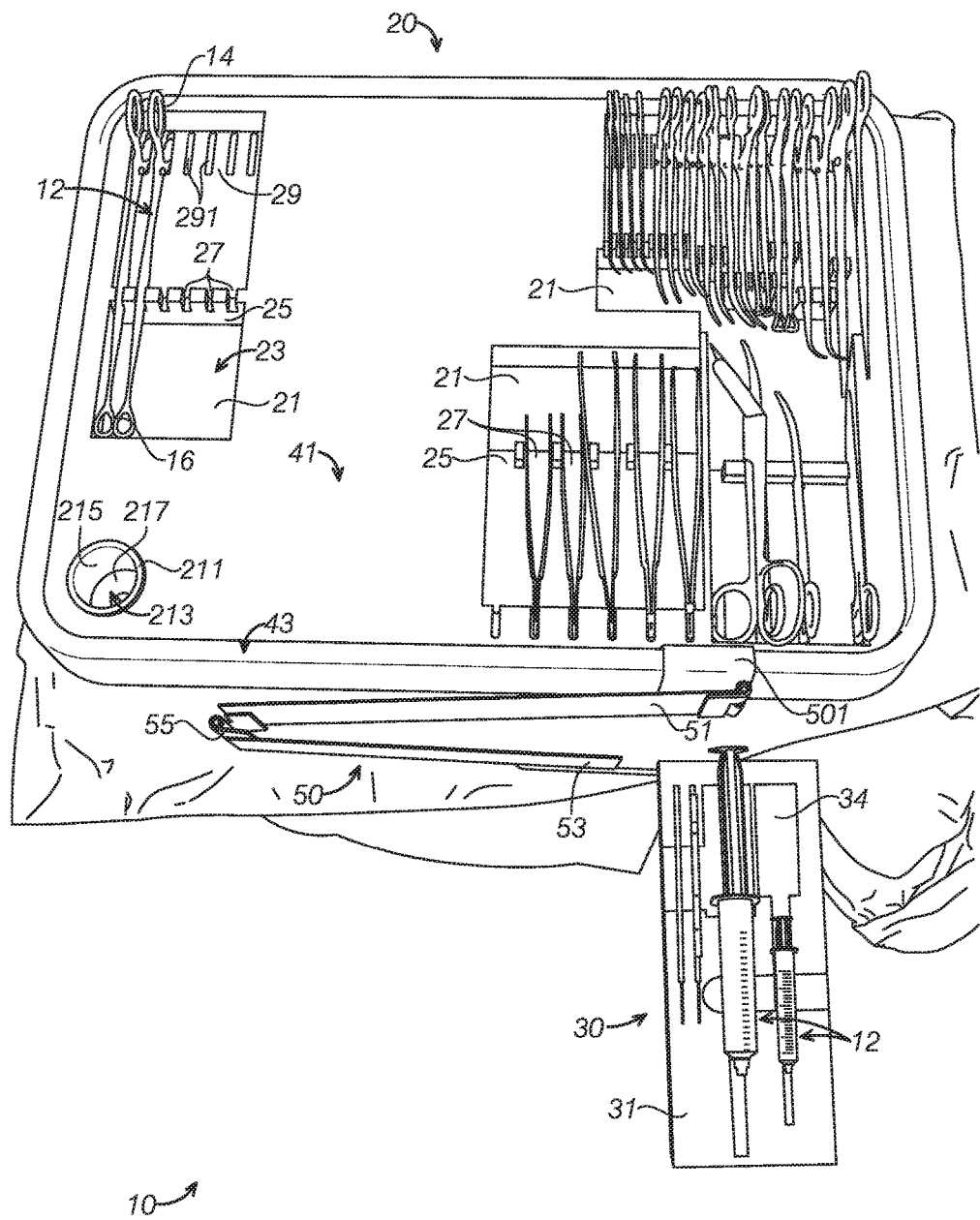
FIG. 1 is a top perspective view of a first tray and a second tray and a linking arm therebetween according to another preferred embodiment of the present invention.

The disclosed trays, systems and methods will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, examples of various trays, systems and methods are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

Overview

FIGS. 1 through 10 depict system 10, a surgical tray system designed to hold necessary instruments for surgical procedures. Each respective tray of system 10 is configured to hold, display, present, or otherwise present in a ready-to-use orientation all, substantially all, or most known or conceivable surgical tools, instruments, or supplies, and particularly those instruments generally understood to be a part of a "general instrument kit".

Each respective tray includes one or more features that, alone or in combination, present, display, or otherwise retain one or more surgical instruments such that the sharp or puncture or cutting end of the instrument(s) are held below the tray's work surface. In this way the user is unable to cut, prick, slice, or otherwise puncture him- or herself on the sharp end of the instrument when that instrument is stored in the tray at a "ready-to-use" perpendicular orientation.

Each tray also holds and displays, for easy access, multiple forceps, knife-handles and retractors, while taking up minimal space on an operating room back table.

Each respective tray is made of rubber, plastic, or metal material that is capable of normal sterilization techniques, and may either be reusable or disposable. Accordingly, each tray may include features to facilitate sterilization, such as being disposed with holes for flow during the sterilization process.

As mentioned above and visible in FIG. 1, the present invention in various preferred embodiments contemplates a two-tiered tray design, which enables a standardized set up prior to any desired procedure where sterilized instruments and supplies are required. The two trays are designed and configured for a specific standardized set up incorporating a number of specific instruments situated in specifically designated locations within system 10.

The design of the two trays and associated method further enables users such as operating room personnel to quickly inventory, count, and account for all instruments and materials/supplies used preoperatively, intra-operatively, and post-operatively. This system of two trays and the method of use thus enables a more accurate and efficient final accounting of all surgical instruments and materials. Although most trays are generally universal in use, there are, in various contemplated alternative and preferred embodiments, some unique tray designs having common features that are optimized for a particular operation, sequence, procedure, and the like.

The precise ordering and location of individual instruments and supplies is defined in a standards or method and procedure manual. As will be well-understood by those having ordinary skill in the relevant art, after the final post-operative accounting, the counted instruments are placed in a contaminated container and transferred to the sterile processing department for re-sterilization according to normal hospital protocols. The sterile processing department, after separate sterilization of each of the two trays and all of the instruments, packages each tray with specific instruments and supplies in a prescribed manner—namely, each instrument has a specific, individual, location in a given tray.

The sterile processing room, in a controlled and sub-sterile environment, pre-packages specific instruments in specific trays and seals the ensemble together for delivery, in a sterile fashion, to the end destination of use (i.e., the operating room). Because this assembly is done in the sterile processing department, should any instrument be dropped or damaged, a replacement can be obtained prior to packaging, thus avoiding waste in the surgery suite, and saving time as well.

All surgical instruments and materials are pre-selected from the surgeon's preference list according to surgical specialty, placed in a transfer cart and delivered from a sterile processing department and/or from the sub-sterile room to the operating room.

Once in the operating room, the system of the present invention—particularly, the two trays replete with surgical instruments and supplies, as applicable, already pre-loaded in specific, pre-designated locations in a given location on either the first or second tray, are then opened in a sterile fashion by the scrub nurse or surgical technician. This eliminates the need for the scrub nurse to organize and place each instrument on a given tray. Thus, system 10 offers significant benefits: in a hectic, busy, urgent or emergency situation, this invention saves time and ultimately lives. In the ordinary course of use, the invention not only saves time, but also provides a greater ability to track, record, inventory, and account for every item in the surgical suite.

System 10, especially when used in conjunction with method 100 as described herein is for use upon the operating room setting with no additional set up time and personnel requirements. System 10 (and corresponding method 100) provides a unique design intended for the purpose of protecting operating personnel and patients from all-to-common sharps injuries preoperatively, intra-operatively and post-operatively.

Such injuries are a major cause of patient and hospital staff injuries, adverse patient outcomes, staff safety and legal liability and damages. System 10 and method 100 purposefully promotes and maximizes patient and staff personnel safety with unique safety designs that greatly reduce or completely eliminate exposure from sharp objects used in surgeries.

System and Devices

Figure 2:
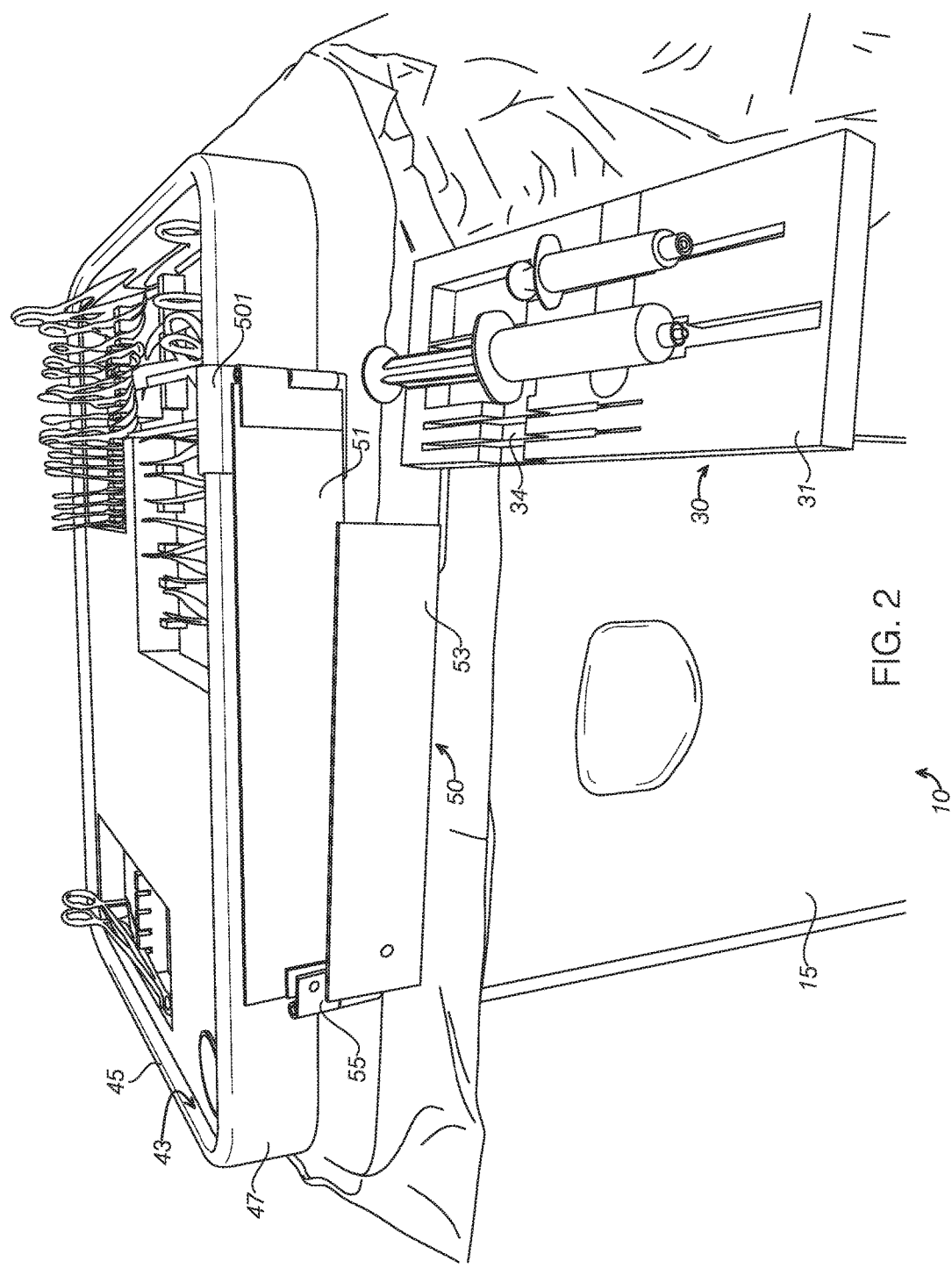
FIG. 2 is a front perspective view of the tray and arm assembly shown in FIG. 1.

With reference to FIGS. 1 and 2, a first preferred embodiment of the present invention is depicted. System 10 consists of a first tray 20 and a second tray 30, which are linked together via an articulating linking member 50, which is preferably implemented as a hinged swing-arm.

First tray 20 is configured for use as a medical surgery tray, holding at least one medical instrument 12 having a handle end 14 and a working end 16. First tray 20 includes at least one substantially flat work surface 41 that comprises a reference plane. An edge feature 43 surrounds the at least one substantially flat work surface 41 whereby edge feature 43 includes an edge feature top surface 45 standing proud at a predetermined positive offset distance from the reference plane. Edge feature 43 comprises at least a work-surface-side wall 47 intersecting the at least one substantially flat work surface 41 at approximately 90-degrees. Edge feature top surface 45 is coupled to the work-surface-side wall 47, wherein the top surface 45 disposes generally parallel to work surface 41 and is further defining the positive offset distance measured from the reference plane.

First tray 20 further includes at least one recessed compartment 21 comprising a bottom surface 23 disposed substantially parallel to work surface 41 and offset therefrom at a negative offset distance. The at least one recessed compartment 21 further comprises a first support truss 25 disposed intermediate to work surface 41 and bottom surface 23. First support truss 25 includes at least one tool-support notch 27 and a cooperating and corresponding second support truss 29 comprising at least one support groove 291 disposed at a negative offset from work surface 41. Groove 291 is further configured so the instrument inserted in the cooperating tool-support notch 27 and groove 291 arranges working end 16 of medical instrument 12 to lie below work surface 41.

The depiction of recessed compartment 21 in FIGS. 1 and 2 is only one possible implementation, and is in no way intended to be limiting. Recessed compartment 21 may be configured in a wide variety of manners to accommodate the full range of surgical/medical instruments 12 that are sharps. Such variations will contemplate changing the placement and size of support truss 25 and 29, as well as the size of tool-support notch 27 and support groove 291. Recessed compartment 21 may include more or fewer support trusses, and may be presented in a variety of shapes, e.g. polygonal, square, rectangular, triangular, circular, semi-circular, etc., as necessary to accommodate any particular medical instrument 12.

As can be seen in FIG. 1, first tray 20 may further include one or more additional recessed compartments 21 that are useable for additional instruments. For example, first tray 20 includes a second recessed compartment 211 separate from the first recessed compartment. Second recessed compartment 211 includes a circular opening 213 in the work surface and having at least one curvilinear sidewall 215 extending therefrom downward intersecting with a bottom-platform 217 recessed in a negative offset from work surface 41 whereby the second recessed compartment configures to accept a fluids container, for example.

Second tray 30 is constructed of identical or similar materials to first tray 20, and varies from first tray 20 primarily in size and configuration of the various recessed compartments. Second tray 30 includes a corresponding at least one work surface 31 defining a reference plane, at least one recessed compartment 34 offset at a negative distance from this reference plane and is configured to selectively hold at least one medical instrument 12 in a position whereby working end 16 is below this reference plane.

First tray 20, second tray 30, and other similarly implemented trays useful with system 10 consist, comprise, or otherwise include, are manufactured, molded, stamped, or machined of, or from, sturdy plastic, metal, composite, or any other material or combination of materials now known or later developed that are coated, painted, rubberized, finished, sealed, or left in a state as a natural result of the process used to create the tray, so long as such materials are useful for use in a surgical environment and are sufficiently durable to withstand the stresses imposed by repeated sterilization processes.

Linking member 50 attaches or otherwise couples to first tray 20 at a first proximal end 51 of the linking support member and selectively attaches or otherwise couples to any additional tray, such as second tray 30, at a second, distal end 53 of the linking support member. Linking member 50 is configured to enable second tray 30 to rotate into and out of a field of sterilization, and is further configured to rotatably move from a first position over first tray 20. In the present embodiment, linking member 50 further includes an intermediate hinge 55 disposed between the distal and proximal ends.

Linking member 50 further is preferably configured to position first tray 20 on an upper plane, or upper tier, relative to second tray 30, which is positioned as a lower tier. Accordingly, second tray 30 is positioned and configured to move relative to first tray 20 such that first tray 20 is above second tray 30 as second tray 30 is brought proximate to first tray 20. Second tray 30 thereby can essentially dock beside and below, or beneath, first tray 20.

Linking member 50 preferably attaches or couples to first tray 20 and second tray 30 in a removable fashion, so as to facilitate break down and ease the process of sterilization of the trays and linking member 50 between surgical procedures. As depicted in the figures, such removable coupling is accomplished by use of various clamps or connectors. However, some embodiments may have linking member 50 permanently or semi-permanently attach to first tray 20 and second tray 30. Such permanent or semi-permanent attachment can be effected by any known or later devised method of attachment, such as adhesives, mechanical fasteners, or molding/embedding during the manufacture of the trays and/or linking member 50.

Figure 3:
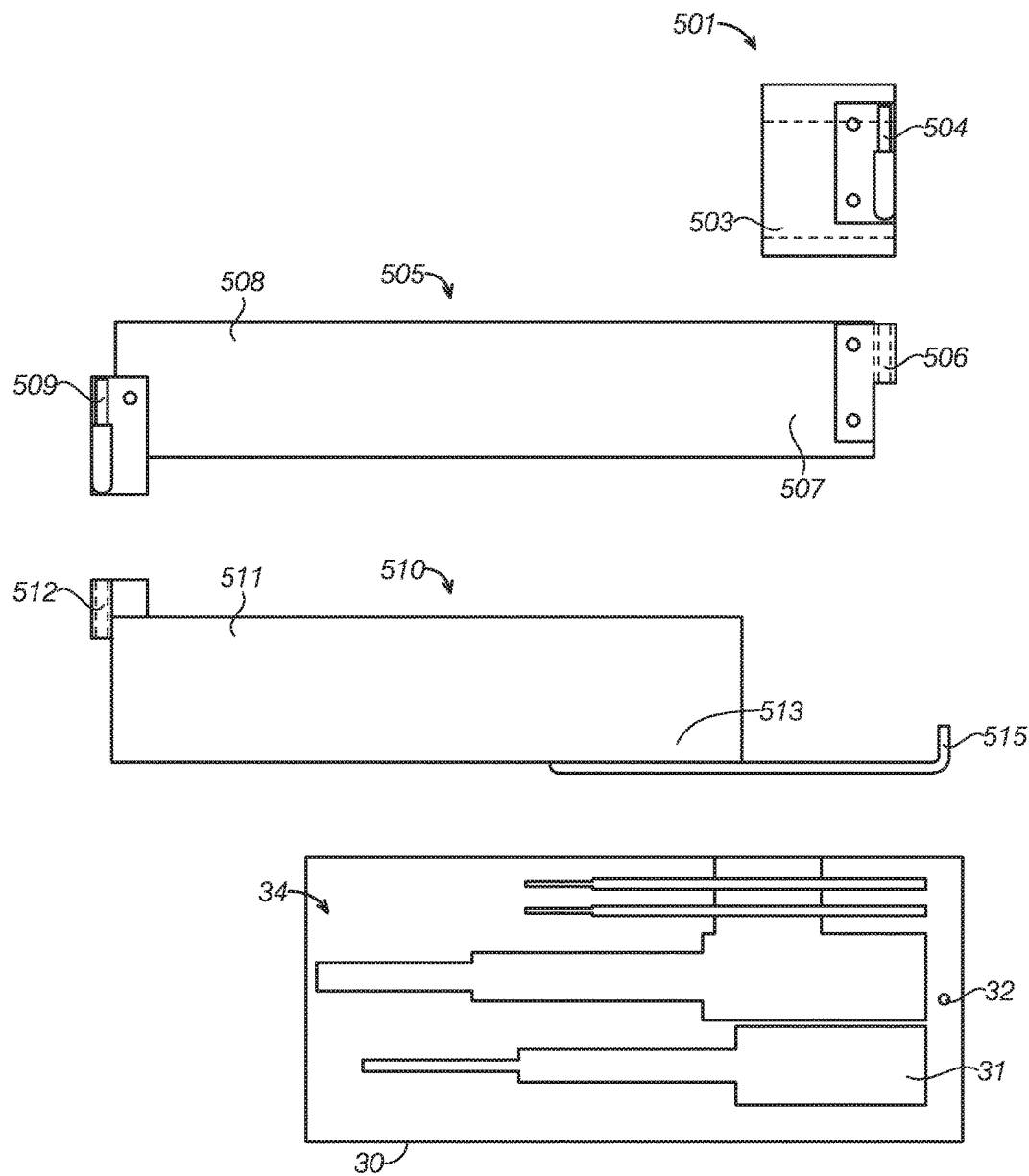
FIG. 3 is an exploded view of the components of the mounting arm assembly and attached tray depicted in FIG. 1, including a bracket, mounting arm and mounting arm-attached tray according to one embodiment of the present invention.

Turning to FIG. 3, one possible implementation of linking member 50 further consists of a swing-aim bracket 501 configured to couple to the work surface 41 of first tray 20. Swing-arm bracket 501 consists of a coupling member 503 configured to engage a portion of first tray 20 sidewall 201 and work surface 41. Coupling member 503 further includes a sleeve 504. Linking member 50 further includes a first arm member 505 comprising a pin 506 disposed on a proximal end 507 whereby the pin configures to slideably engage sleeve 504 and whereby the pin enables the sleeve to rotate. First arm member 505 further comprises a distal end 508 having a first-hinge end 509.

Linking member 50 further includes a second arm member 510 comprising a cooperating second-hinge end 512 configured to hingeably engage first-hinge end 509 and disposed on a proximal end 511 of second arm member 510. Second arm member 510 further includes a distal end 513 having a post 515.

While linking member 50 and its constituent components are depicted in the example embodiment as an articulated arm with one center pivot point, this is in no way intended to be limiting. Linking member 50 can be implemented using any design that facilitates second tray 30 to move with respect to first tray 20, thereby allowing second tray 30 to be moved into or away from the surgical field. For example, some such implementations may have a single member which pivotably attaches on a proximal end to first tray 20 and a distal end to second tray 30, with no intermediate pivot point. Other examples may include a linking member 50 with multiple pivot points, or likewise configured with an accordion-style folding mechanism, thereby allowing second tray 30 to telescope away from first tray 20, in addition to or in the alternative to pivoting.

Linking member 50 and its various components are preferably constructed from a durable material such as metal or plastic that can be readily and easily sterilized, and which is robust enough to withstand multiple sterilization process cycles. Alternatively, linking member 50 can be constructed from any other similarly suitable material or combination of materials now known or later developed.

In this way, system 10, having second tray 30, uses linking member 50 to position first tray 20 and second tray 30 relative to each other. Second tray 30 is configured to receive distal end 513 of linking member 50. Accordingly, second tray 30 includes a post-receiving hole 32 configured to rotatably receive post 515 of second arm member 510. This allows second tray 30 to be moved from a first position to a second position, relative to the location of first tray 20.

Optionally, any additional plurality of trays can be provided, and each includes any combination of features, alone, or combined as described with respect to first tray 20 and second tray 30, above. Or, additional trays can include features not discussed herein wherein those features would be well understood by those skilled in the art at the time of this invention. Linking member 50 may be reconfigured to accommodate one or more additional trays, in addition to second tray 30. Alternatively or additionally, one or more additional trays could be mounted separately to first tray 20, either directly or via additional linking members 50.

System 10 further may include in some embodiments at least one specialized surgical drape 400. Surgical drape 400 has at least one predefined area 410 printed or otherwise demarked thereon. Surgical drape 400 is configured to cover a back table in the operating room. The at least one predefined area 410 cooperates with a method of arranging supplies or instruments thereon. Thus, drape 400 enables and indicates the systematic placement of at least one surgical instrument or supply, and also facilitates pre- and post-operative audit counts.

Figure 4:
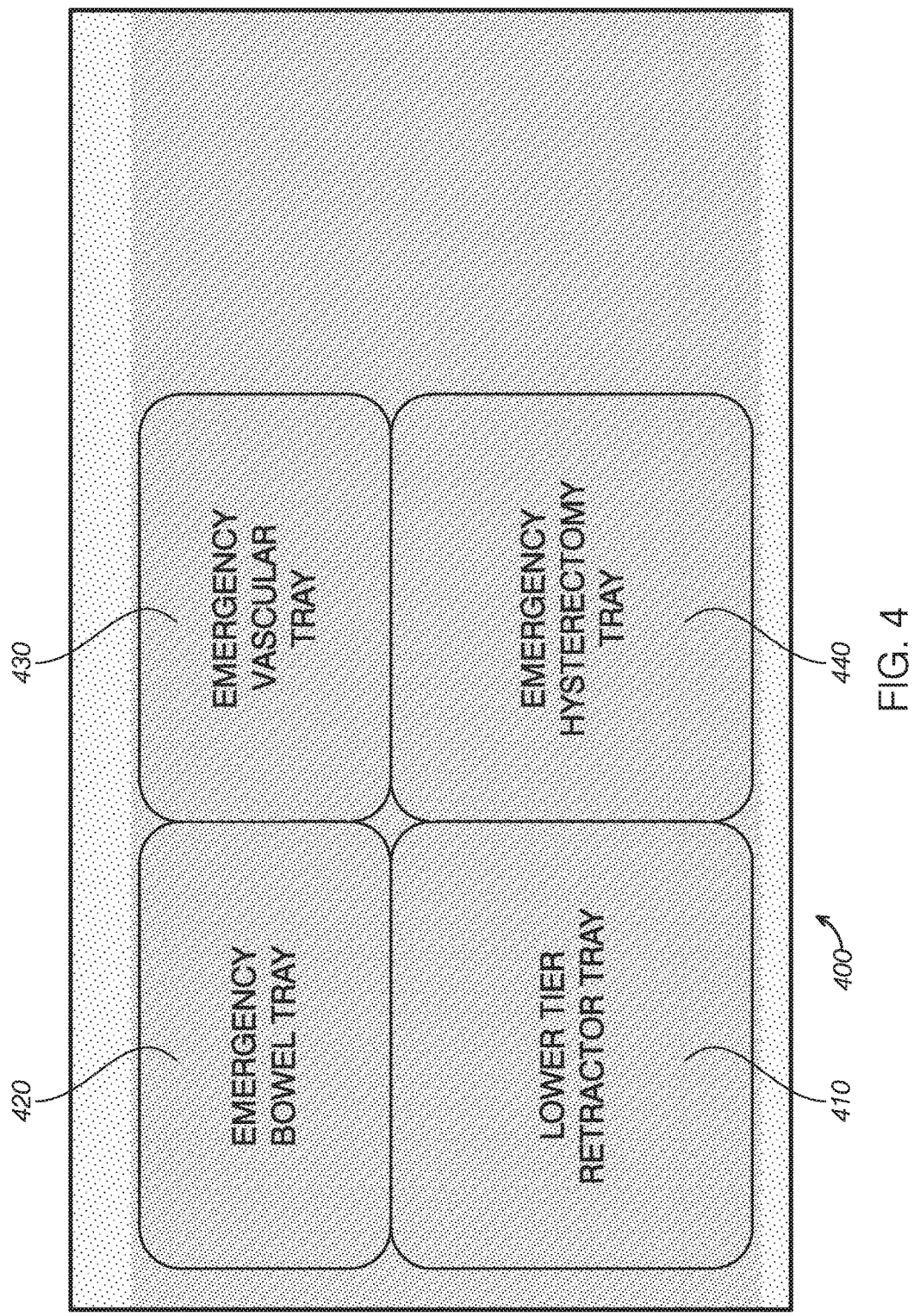
FIG. 4 is a top view of a back-table pre-marked drape according to one preferred embodiment of the present invention.
Figure 5:
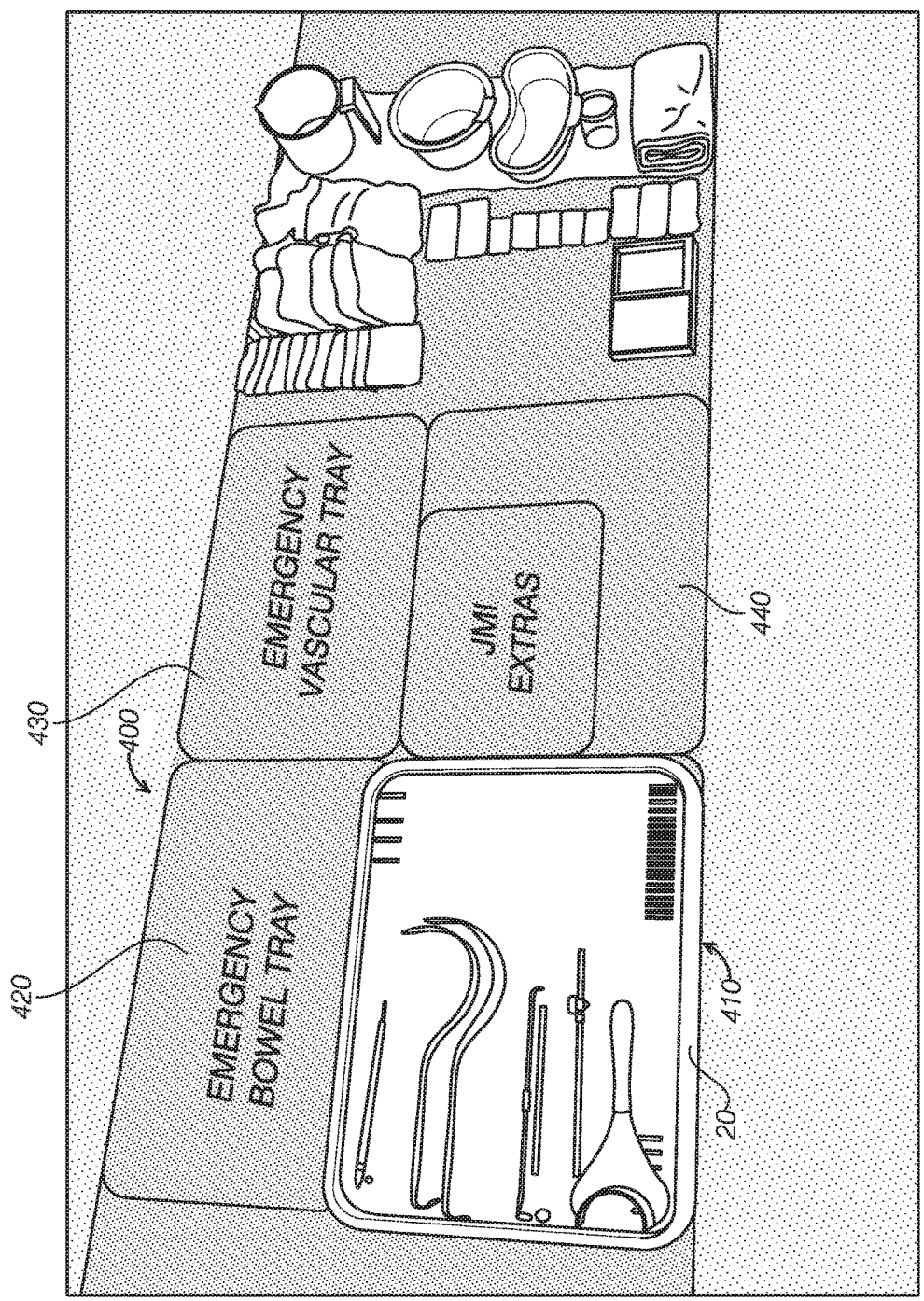
FIG. 5 is a top view of the back-table drape of FIG. 4 and shows a tray according to an embodiment of the present invention along with surgical supplies and instruments located on the pre-marked back-table drape.
Figure 6A:
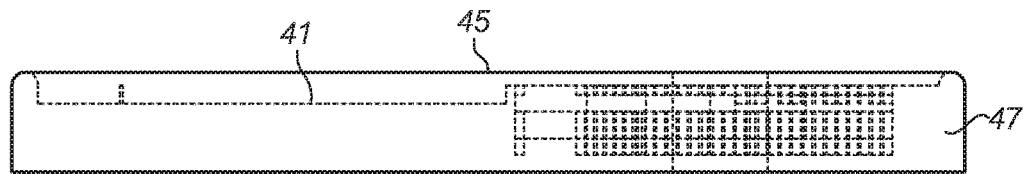
FIG. 6A is a front view of a second example tray, calling out similar features to those of the example first tray depicted in FIG. 1.
Figure 6B:
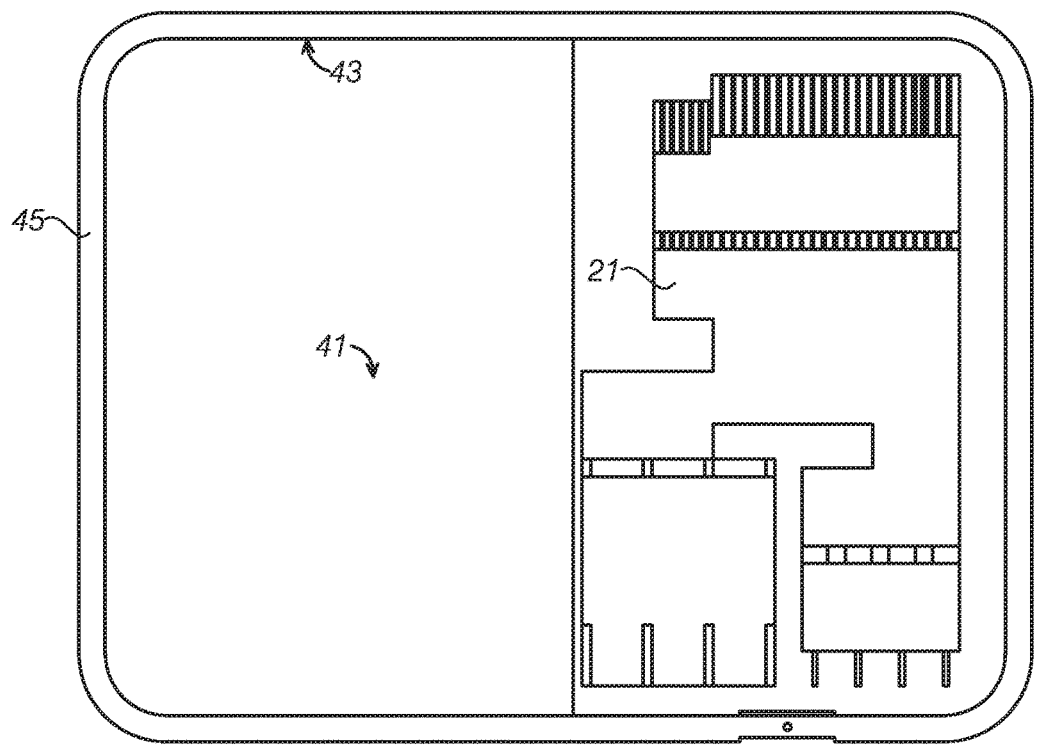
FIG. 6B is a top view of the tray of FIG. 6A.
Figure 6C:
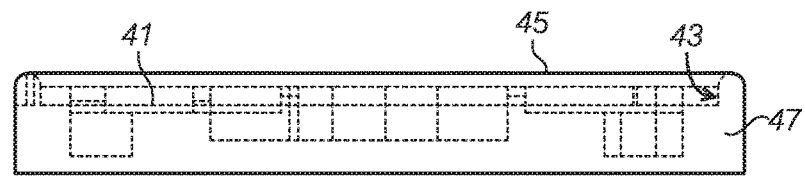
FIG. 6C is a left-side view of the tray of FIG. 6A.
Figure 6D:
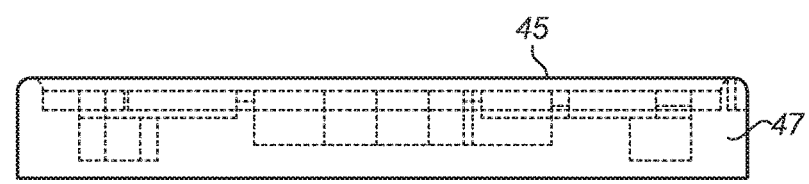
FIG. 6D is a right-side view of the tray of FIG. 6A.

Referring now to FIG. 4, a pre-printed back table surgical drape 400 with pre-demarked areas 410 to 440 is depicted. According to one embodiment of the present invention, surgical drape 400 is opened using sterile technique and placed on the back table ready to receive any number of trays of the present invention along with other surgical materials. These items are placed in the specified locations denoted by the appropriate areas 410 to 440 on the back-table surgical drape 400 according to the requirements for the specific surgical procedure. Exact placement may be further defined in unique procedure manuals. Surgical drape 400 is manufactured using conventional techniques and materials known in the art for the manufacture of surgical drapes to be used on instrument stands.

While surgical drape 400 is depicted in FIG. 4 as possessing four areas 410 to 440, this is not intended nor, should it be taken to be limiting; surgical drape 400 may have fewer or greater numbers of pre-demarked areas, to accommodate a variety of surgical procedures. Furthermore, the pre-demarked areas of surgical drape 400 could be customized to specific surgical procedures, wherein surgical drape 400 would be specifically configured for one or a few procedures, and thus possess only those specific pre-marked areas that are pertinent to the procedures for which surgical drape 400 is tailored.

The instruments used intra-operatively, also called "sharps" in the relevant art, are each individually placed in second tray 30 by the surgical technician or scrub nurse into a unique designated position. Second tray 30, when needed for use, is moved from the first, retracted position, to a second, extended position. The second, extended position is within the sterile field. Second tray 30 swings or otherwise is angled to and presented to the sterile field, and is used to deliver or receive sharps. When this specific action is completed, second tray 30 is returned to the first, retracted position below the surgical stand. This process may be repeated several times during a single procedure. At the end of a surgical procedure, the sharps instruments contained in second tray 30 are counted and removed and placed in approved sharps containers and disposed of per hospital protocol.

Second tray 30 of system 10 is placed on back-table drape 400 in a pre-designated standardized location as set forth on the mapped back-table drape 400. Instruments delivered to the operating room are then counted and accounted for per protocol.

In another preferred embodiment, system 10 can be adapted for organizing a plurality of medical instruments 12 and a plurality of surgical supplies in a sterile operating room in preparation for a procedure, operation, or surgery. In this embodiment system 10 includes a first tray 20, a second tray 30, an optional third tray 60 (seen in FIG. 10), and a linking member 50 adapted to couple to the first tray 20 to any additional tray. One contemplated variation or embodiment of third tray 60 is designed specifically to contain any extra instruments that may be needed during a particular surgical procedure. Typically, this third tray 60 is used to introduce instruments or supplies coming from the back table and being placed into the sterile field. Third tray 60 is preferably equipped with a flat space 62 to allow including surgical and/or medical supplies that do not need to or otherwise fit into a recess designed to accept medical instruments 12. Third tray can optionally include at least one slotted recesses 64 that are pre-designated for specific, individual items, supplies, or instruments. This enables quick view counts and safe, easy access for relaying instruments during surgical procedures.

The present invention contemplates a system of specialized trays adapted for specific, predetermined surgical procedures. These trays share common traits, characteristics, and elements as just described above, but are further customized to hold specific instruments based on the intended use during a given procedure. Some examples of these specialized trays are now described, below.

Figure 8:
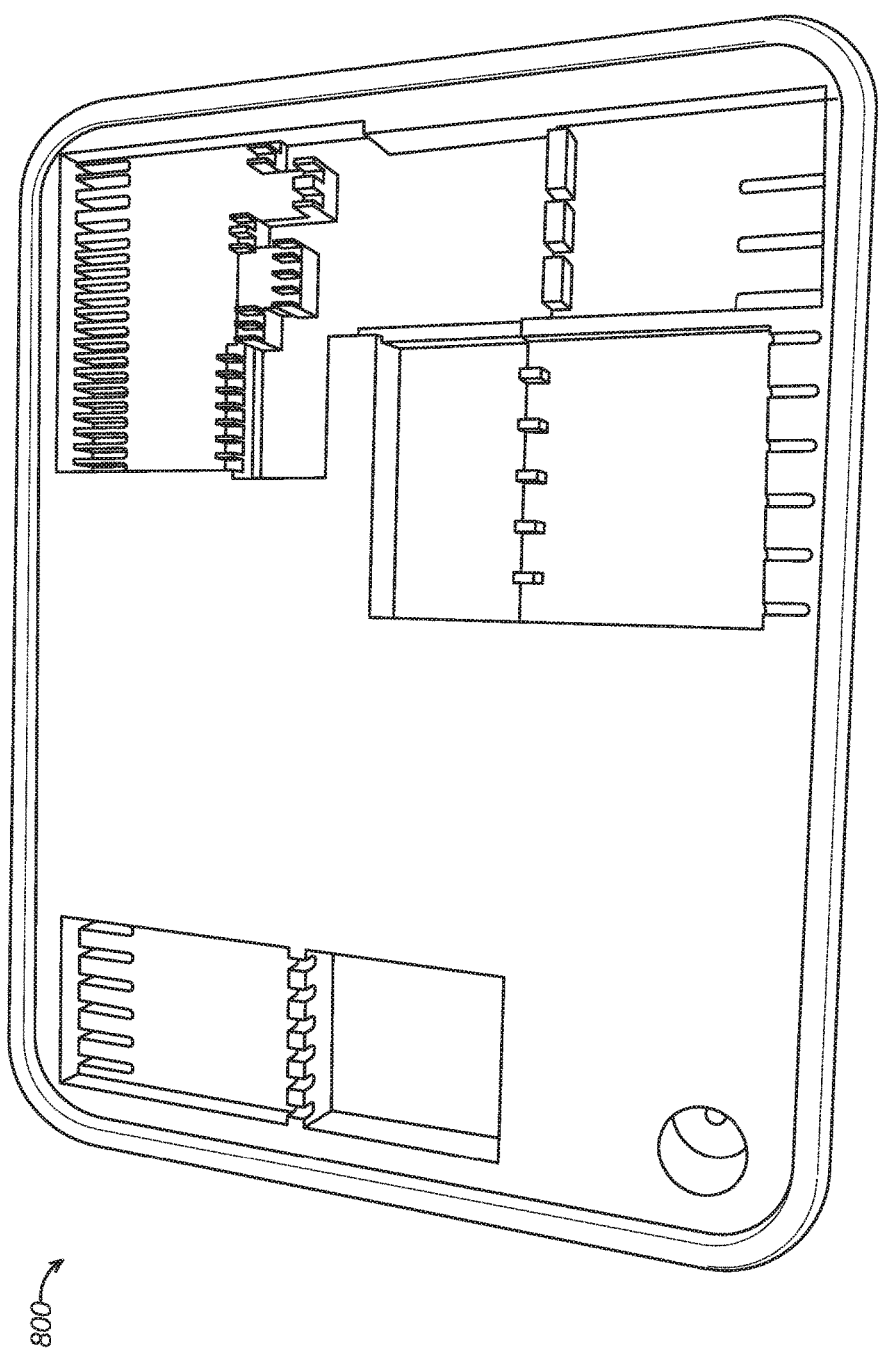
FIG. 8 is a top perspective view of the tray of FIG. 1, without instruments arranged therein, further illustrating the recessed slots.

General Surgery Services:

Adapted for use with general surgery services, the present invention includes a system comprising a plurality of devices. Example trays are depicted in FIGS. 6A to 10. These devices include:

A universal major tray, similar to first tray 20 depicted in FIGS. 1 and 2, and shown in FIG. 8 as tray 800, having features that prevent sharp injuries as described above. Tray 800 is further configured to arrange a minimum number of instruments necessary for specific procedures. It readily couples to a standardized Mayo stand 15 by a recessed guide underneath the tray and works in conjunction with a second tray 30 in a two-tier configuration. Further, it accepts a third tray 60 with a recessed sharps-slot feature. This configuration minimizes scrub nurse set up time and provides an easy view for a continuous running count of instruments and retractors. Further, this major tray 800 includes a recession and individual slots to accept a standardized number of instruments and retractors and orient them in the ready position for easy relaying to the surgical field.

Figure 7:
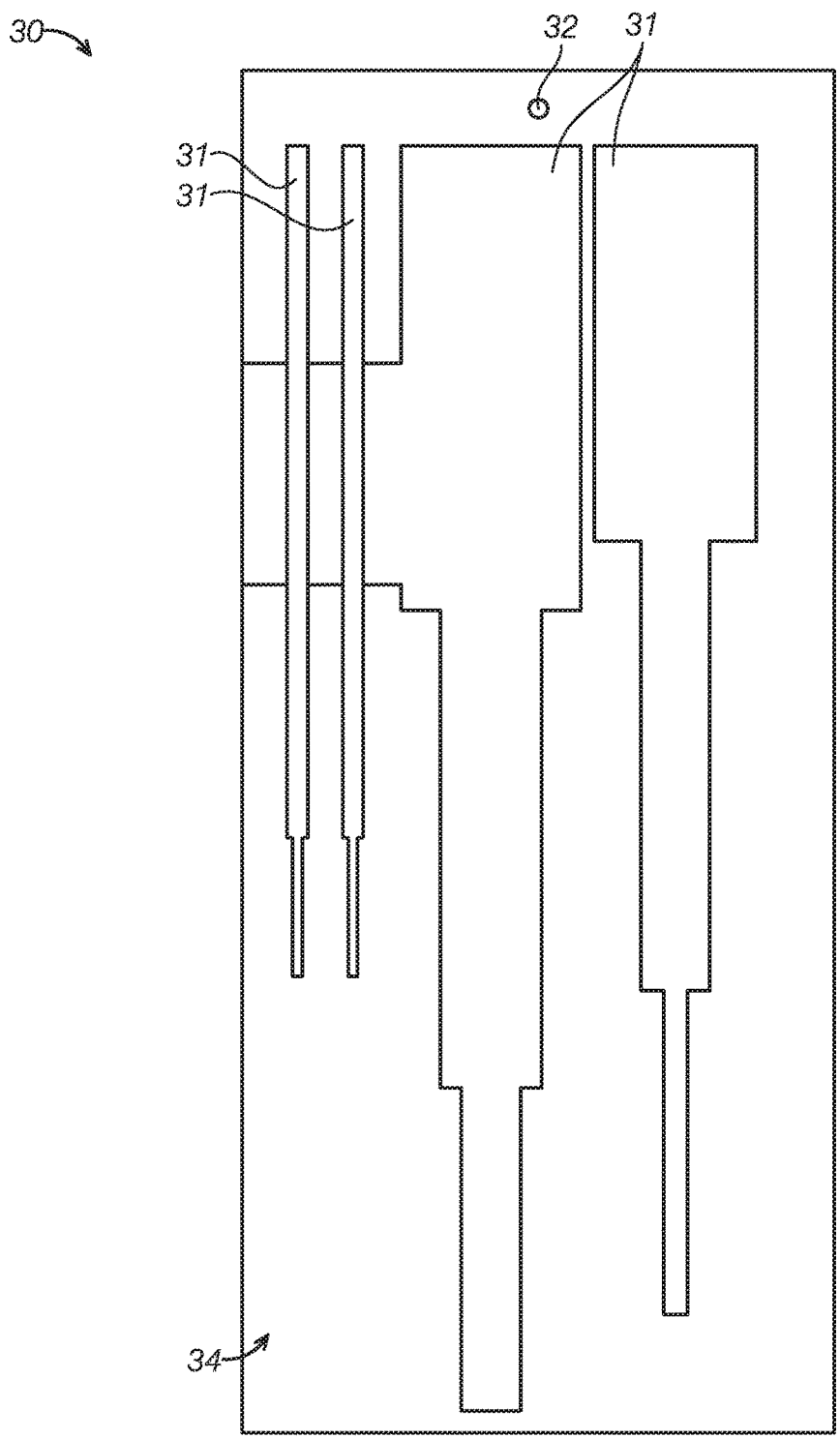
FIG. 7 is a top view of an example second tray as depicted in FIG. 1.

System 10 may further include a minor tray, presented in detail in FIG. 7 which depicts second tray 30 as described above. Second tray 30 also includes the afore-described sharps prevention configuration, as well as containing the minimum number of instruments necessary for specific procedures. Second tray 30 adapts to a standardized minor surgery Mayo stand 15 by the recessed guide underneath the tray. It works in a two-tier arrangement using linking member 50, as a lower tier tray, and preferably further includes the sharps-slot feature.

In a similar manner, specialized trays having features to orient the surgical instruments in a "ready" position, and further configured to hold only the specific supplies, retractors, and instruments associated with the respective specialized surgical procedure are contemplated. Some contemplated tray systems include, but are not limited to, a Common Bile Duct Tray, a Laparoscopy tray, a Laparoscopic Cholecystectomy Tray, a General Surgery Closing Tray, an Orthopedic Services System including a Major Ortho Tray and a Minor Ortho Tray, an Open Shoulder Tray, an Arthroscopy Tray, a Podiatry Services system including a Podiatry Tray, an Ob/Gyn Services System including the Laparoscopy Tray, an Abdominal hysterectomy Tray, a Vaginal Hysterectomy Tray, a Laparoscopic Hysterectomy Tray, a Dilation and Curettage Tray, and a Cesarean Section Tray.

Other specialized tray systems include a Vascular Services system including a Major Vascular Tray, a Minor Vascular Tray, and a Vein Ablation Tray. Yet others include a Urology system including an Open Prostatectomy Tray, An Ear Nose and Throat system including a Myringotomy Tray, a Nasal Septoplasty Tray, a Tracheostomy Tray, a Stapedectomy Tray, a Major Plastics Tray, and a Minor Plastics Tray.

Each of these aforementioned trays share similar characteristics including materials, construction, the ability to be re-sterilized, having sharp-safe features, and including individual slots for pre-determined instruments. Thus, each of the aforementioned trays is useable as a first tray 20 and/or second tray 30 with system 10, and method 100. FIGS. 6A through 6D depict some common elements the aforementioned trays may possess. However, it will be appreciated by persons skilled in the relevant art that the general configurations of the aforementioned trays with respect to flat areas and recessed compartments, as well as the size and configuration of the recessed compartments, can and will vary depending upon the unique needs of any given surgical procedure. These variations are contemplated and do not depart from the disclosed invention.

The trays work with system 10 and method 100 disclosed herein, including embodiments of method 100 for inventorying instruments both pre-, intra- and post-operatively, for example. The associated FIGS. 6A to 10 illustrate some of these contemplated specialized trays made in accordance with the spirit, scope, and principles of the present invention as described herein.

FIGS. 6A through 6D depict a variation of first tray 20, with a broader work surface 41 for accommodating more surgical materials other than sharps. Specifically, FIGS. 6A through 6D provide detailed views of the geometries and features of the tray. It should be appreciated that these features are generally common to all trays that are useable with system 10; however, other trays that include fewer of the features depicted in FIGS. 6A through 6D may equally be usable with system 10.

Figure 9:
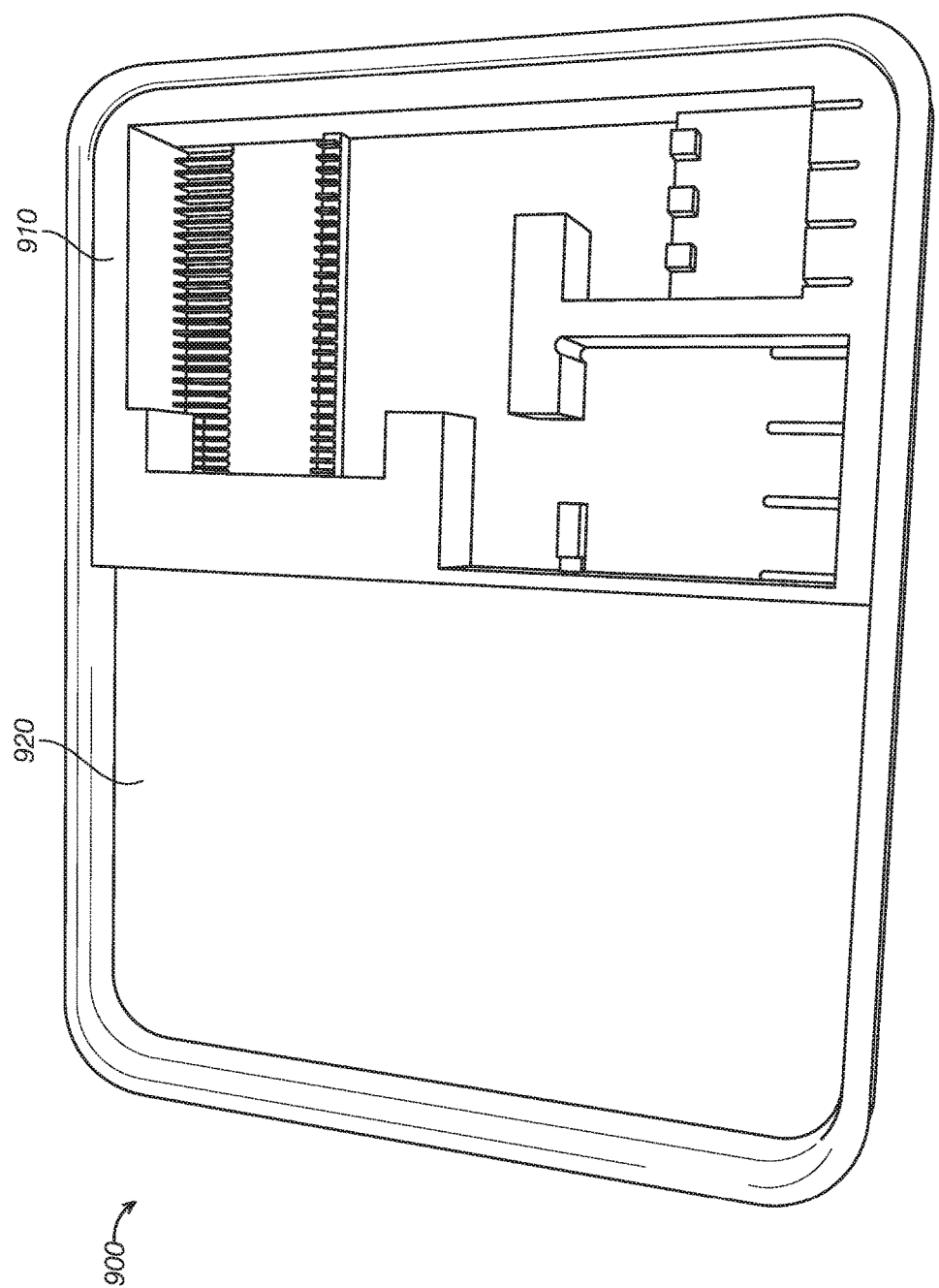
FIG. 9 is a top perspective view of another example tray according to the present invention.

FIG. 9 depicts a tray 900 that includes a recessed compartment 910, similar in configuration and features to the recessed compartment 21, as well as a flat work area 920, which is suited for surgical procedures where materials that do not fit into a sharps-configured recessed compartment 910 can be placed. Examples of such materials may include bandages, suture material, staples/staplers, adhesives, medical devices, or any other similar materials that are known to be needed in various surgical procedures.

Figure 10:
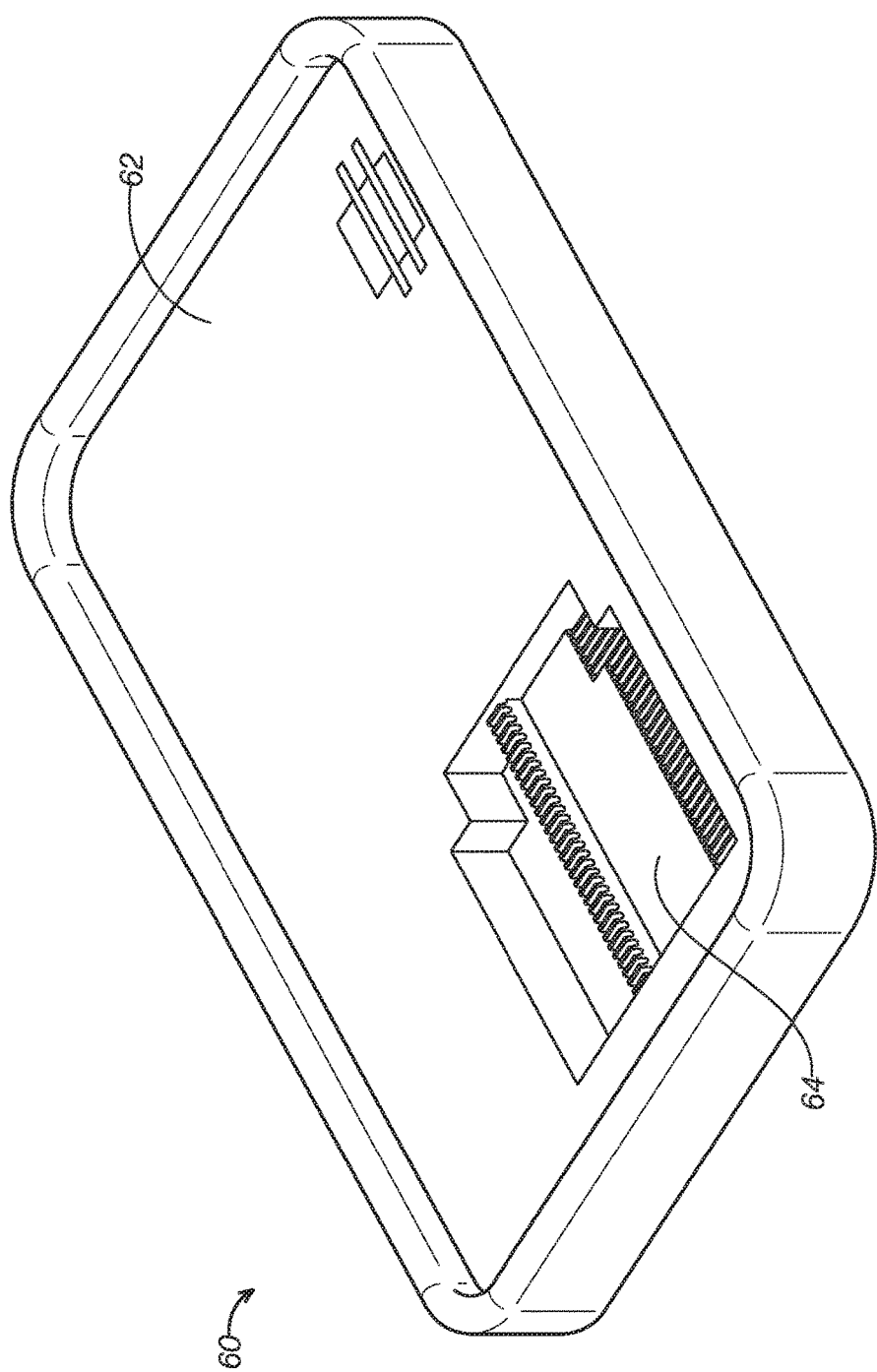
FIG. 10 is an offset top perspective view of a tray according to another preferred embodiment of the present invention.

FIG. 10 depicts yet another possible tray configuration, third tray 60, which can be used for extras or auxiliary materials in general surgical procedures. Similar to FIG. 9, third tray 60 includes a work area 62 for auxiliary materials in addition to at least one recessed compartment 64.

Figure 13:
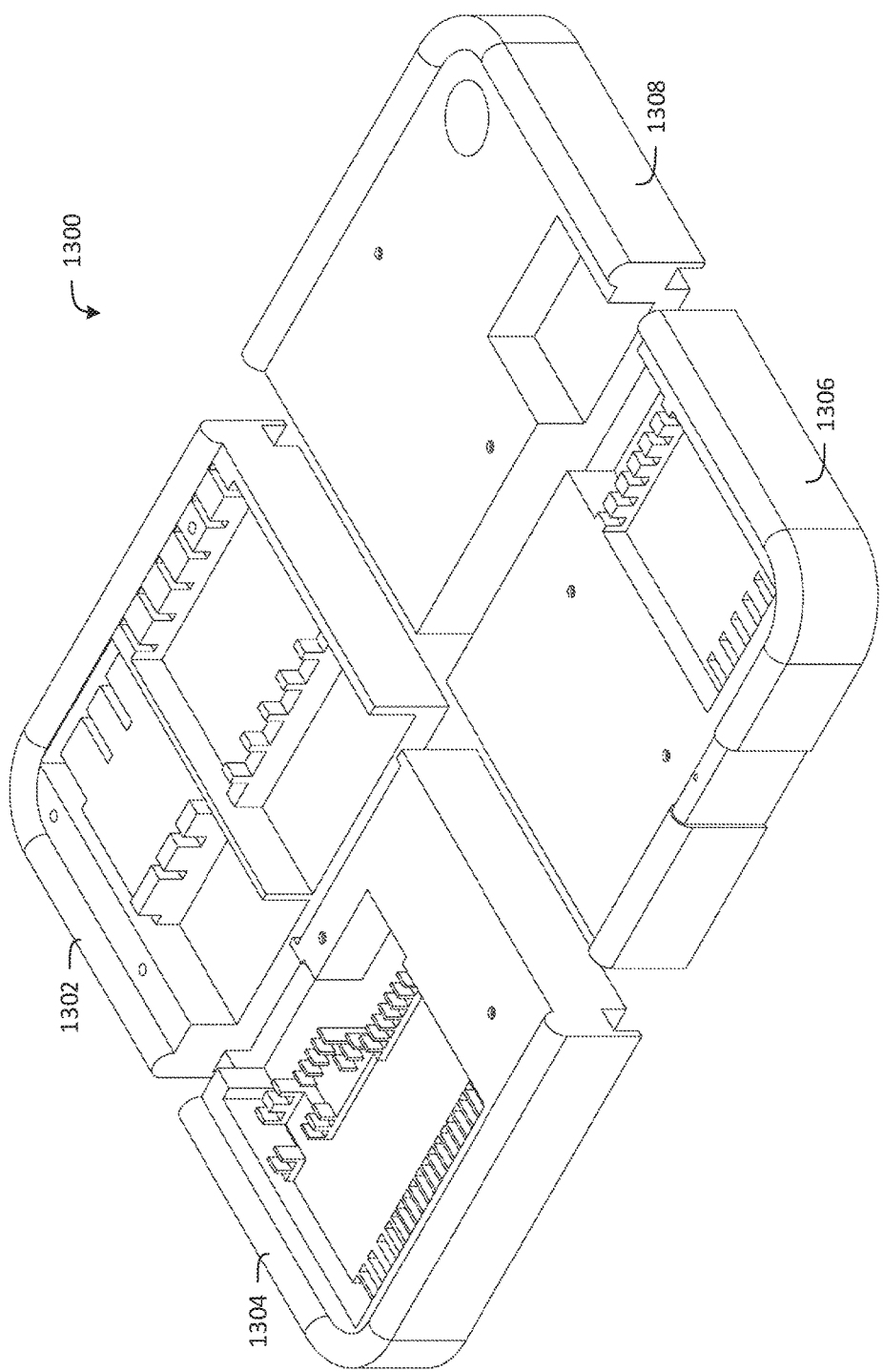
FIG. 13 is a perspective view of another example tray according to another preferred embodiment of the present invention, showing the tray separated into modular components.

FIG. 13, finally, depicts still another possible tray configuration, modular tray 1300. Modular tray 1300 is comprised of a first quadrant 1302, second quadrant 1304, third quadrant 1306 and fourth quadrant 1308. Each of the four quadrants is designed to interlock with the other quadrants so that modular tray 1300 can be configured and reconfigured into different layouts to accommodate the specialized needs of a variety of different surgical procedures. The quadrants interlock using any interlocking mechanism that is known or later developed in the relevant arts that allows modular tray 1300 to be securely assembled and is capable of withstanding sterilization. Moreover, it should be understood that although four quadrants are depicted, this is not in any way intended to be limiting. Fewer or more sections could be implemented to create modular tray 1300 without departing from the disclosed tray.

These specific examples, however, should not be viewed as limiting. Further, features on one specific tray should be understood to be included on other trays, even if those specific features are not shown in the drawing. Further still, features, elements, and components can be combined in any combination.

Method

The present invention further contemplates a method 100 using the system and devices described above. The method enables efficient, reliable, repeatable, and accurate set-up, use, and cleanup of a surgery replete with all necessary instruments and supplies. Method 100 as depicted in FIG. 11 describes the general flow of preoperative preparation, delivery, surgery, and postoperative procedures involved with the use of system 10, including steps for organizing a plurality of surgical instruments and a plurality of surgical supplies in a sterile operating room in preparation for a procedure, operation, or surgery.

Figure 11:
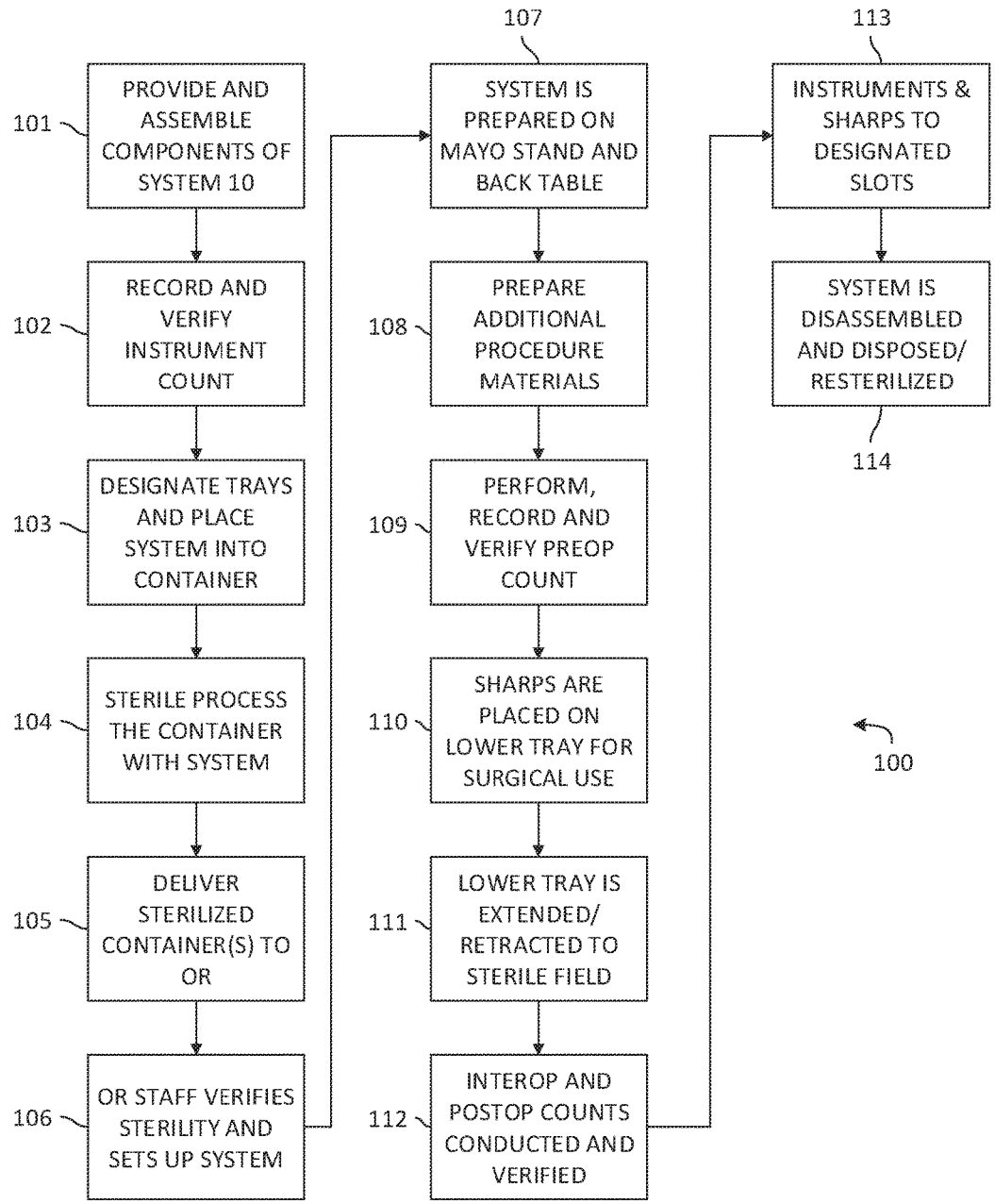
FIG. 11 is a flowchart depicting a method useable with the system of the present invention.

With reference to FIG. 11, method 100 begins by providing and assembling various components of system 10 described above in step 101. Step 101 includes providing a tray system and associated components such as the swing-arm described above, a back-table drape with mapping as described above, and a sharps container system. Previously cleaned medical instruments 12 necessary for various surgical procedures are placed into specific slotted mapped locations in a first tray 20 and, in some instances, a second tray 30. As with medical instruments 12, the trays also are previously cleaned, although some embodiments may clean instruments 12 in place in a tray, as a single unit. The various components of system 10 are then assembled as recommended by established procedures and manufacturer's recommendations.

In step 102, the component instruments of assembled system 10 are counted, the count is recorded on a count sheet, and verified against the count sheet as well as the various mapped slots for the component instruments. A first tray 20 and second tray 30 as part of system 10 may be designated as upper tier tray and lower tier tray, respectively.

The designated trays with their slotted instruments, the count sheet, and other components of system 10 are placed into one or more containers for sterilization in step 103. In the preferred embodiment, a single container containing all components of system 10 is sterilized. However, in some embodiments, medical instruments 12 as well as the tray could each be sterilized separately, following which medical instruments 12 are placed into the tray while still in a sterilized area, and sealed for storage and subsequent delivery to the operating theater prior to a procedure. As discussed above, each tray may be implemented with a variety of different layouts of recesses to accommodate the varied types medical instruments 12 that would be useable with various procedures. Thus, a variety of trays and associated instruments 12 may be provided and kept ready for corresponding medical procedures.

Following insertion into the container(s), the container(s) are sterilized in step 104 with the enclosed system 10 per the policies and requirements of the sterilizing facility. Any appropriate method of sterilization may be utilized. Once sterilized, system 10 can be stored until needed. Once needed for its intended procedure, the sterile container(s) with system 10 are delivered to the operating room in step 105.

Medical instruments 12 in place in their various trays are delivered as complete and sterilized units to operating rooms. Where a surgical procedure may not use all instruments in a given tray, all slots should nevertheless be filled; during the surgical procedure, those tools that are unused are simply left in their given tray.

At the start of a given medical procedure, in step 106, the operating room staff verifies that the integrity and sterility of the container(s) and contained system 10 complies with facility policy, and proceeds with setting up the operating room with system 10. The components of system 10 are opened on the clean surface in a sterile fashion and setup using approved sterile technique. The various trays, including first tray 20 and second tray 30, are opened and dispersed upon suitable stands within the designated sterile area using national operating room standards of sterile technique. Preferably, all positions for medical instruments 12 in first tray 20 are filled, which makes visual inspection during pre- and post-operative counts for verification of the presence of all medical instruments 12 easy. A pre-marked surgical drape 400 can be placed on a designated back table, and trays 20, 30 may be initially placed upon drape 400 in the appropriate pre-marked areas (e.g. areas 410 to 440). The mayo stand(s) to be used is/are draped using sterile technique. All operating room materials pertinent to the surgical procedure are placed on a clean surface.

Once system 10 is deployed from its container(s), in step 107 tray 20 and tray 30 are prepared to the mayo stand 15 and back table. The designated upper tier tray is placed upon the mayo stand 15. First tray 20 is thus removed from surgical drape 400, and placed upon mayo stand 15. One or more medical instruments 12 are already situated and secured in a ready position within the upper tier tray to be relayed to the person performing the operation with no further manipulation of the instruments. Once so positioned, the upper tier tray is coupled to a lower tier tray, by using a swing arm bracket, an embodiment of linking member 50. Instruments immediately needed for the procedures are placed into the designated lower tier tray, to be used for passing instruments and materials into the sterile operating field.

Any remaining countable items, such as sponges, needles, sutures, etc., are prepared in step 108, typically to the mapped back-table drape 400. The sharps container system for system 10 is also placed onto the back-table drape 400, and those countable items that are sharps are placed into the container system in pre-designated locations. Also in step 108 other necessities such as one or more basins such as disposable basins and/or large basins for temporary use are placed into either mapped areas on drape 400 or appropriate stands, as determined by procedure protocols.

For purposes of implementing and using system 10, first tray 20 may be designated the upper tier tray to be used linking member 50, to a second tray 30. It should be appreciated by the reader that the designation of a particular tray as first tray 20, and correspondingly as the upper tier tray, where there are a plurality of trays in the operating theater is essentially determined by the nature of any particular surgical procedure. In the course of a sufficiently complex operation, it is possible that multiple trays may in turn, in an iterative fashion, be designated first trays.

In the final pre-operative step, the initial count is performed, recorded and verified in step 109. Per national operating room procedural standards, prior to commencement of a surgical procedure and prior to the "time out", all countable surgical instruments and materials to be used during a surgical procedure are to be counted verbally and visually by the scrub nurse and circulating nurse. By seeing that all positions for medical instruments 12 are filled in any given tray, the nurse or tech charged with the count has an immediate visual signal whether any particular tool is missing. Medical instruments 12 are thus situated in a ready position to be relayed in a standardized method from their respective, predetermined locations.

Following completion of step 109, system 10 is ready for procedure commencement.

In step 110, any needed sharps such as needles, syringes, knife blades, etc., are placed onto appropriate positions on the lower tier tray, along with all surgical instruments to be relayed to the surgeon intra-operatively from the respective first tray 20 or second tray 30 upon the surgeon's request, with positions between first tray 20 and second tray 30 shifting with respect to each other as materials/instruments 12 are needed. Materials/instruments 12 are passed to/from the sterile field by extending/retracting the lower tier tray in step 111. The lower tier tray can be placed outside a sterile field by moving the lower tier away from the upper tier tray by use of linking member 50.

In sterile fashion (that is to say that an item has been sterilized by a sterile processing department or rendered sterile by the manufacturer, and presented or delivered to the operating room as sterilized and ready for sterile operations and/or procedures), second tray 30 (and subsequent trays, if present) can be removed from back drape 400 and exchanged for first tray 20 on the mayo stand.

Once the surgeon completes use of a sharps instrument, the instrument may be placed on the lower tier tray in a pre-designated slot. The entire lower tier tray with the used instrument is then returned to the scrub nurse, facilitated by linking member 50. At any time intra-operatively the lower tier tray, which is attached to the upper tier tray on the Mayo stand 15, may be easily retracted back below the Mayo stand 15 to its pre-designated position, away from the sterile operating field, thus preventing sharps exposure and injuries.

Any non-sharp instruments relayed to the surgeon are placed in the sterile field where the scrub nurse will pick up the instrument and return the instrument to the pre-designated instrument slot on its corresponding tray.

In step 112, inter-operative and post-operative counts are conducted and verified. Accountable items may be counted at any time during the surgical procedure at the request of any person involved in the surgical procedure. Closing counts are performed per protocol of all accountable instruments, sharps, sponges and other disposable items not included in this system. Thus, the medical provider involved with the surgery can be notified immediately of any discrepancies and take corrective action per hospital protocol. At the close of procedure, all items are counted by the scrub nurse and the circulating nurse to make certain all items are accounted for and placed in their pre-designated position. This is the Closing Count Procedure. The number of counts of surgical items and materials varies per surgical procedure (i.e. Uterine Count, Major Abdominal Vascular Count, Open Heart Count), as would be well understood in the art.

Upon announcement of closure of the surgical procedure, in step 113 all instruments are returned to their mapped positions on first tray 20, second tray 30, and any additional tray as appropriate. Sharps and surgical materials, and any additional items brought to the field during the operation, are placed on the drape 400 and sharps container as appropriate. This step may be conducted prior to the closing count procedure, to facilitate a quick visual inspection and verification of the count of all instruments and materials.

Following the final count, system 10 is disassembled, used non-useable materials are disposed of in an appropriate fashion, and all instruments, trays, and associated reusable equipment is sent for cleaning and resterilization in step 114. The upper tier tray, swing arm and lower tier tray are removed from the mayo stand and placed into the previous sterile container to be sent to the sterile processing department for reprocessing per hospital policy, along with medical instruments 12, any additional trays, and any other reusable equipment. The sharps container is closed to contain the used sharps and disposed of in a hospital designated biohazard sharps container. Back-table drape 400 and other disposable items are discarded into designated biohazard receptacles per hospital policy.

It will be understood that method 100, while being performed in substance as described above, may have minor variations that are dependent upon the specific procedure being conducted.

Figure 12:
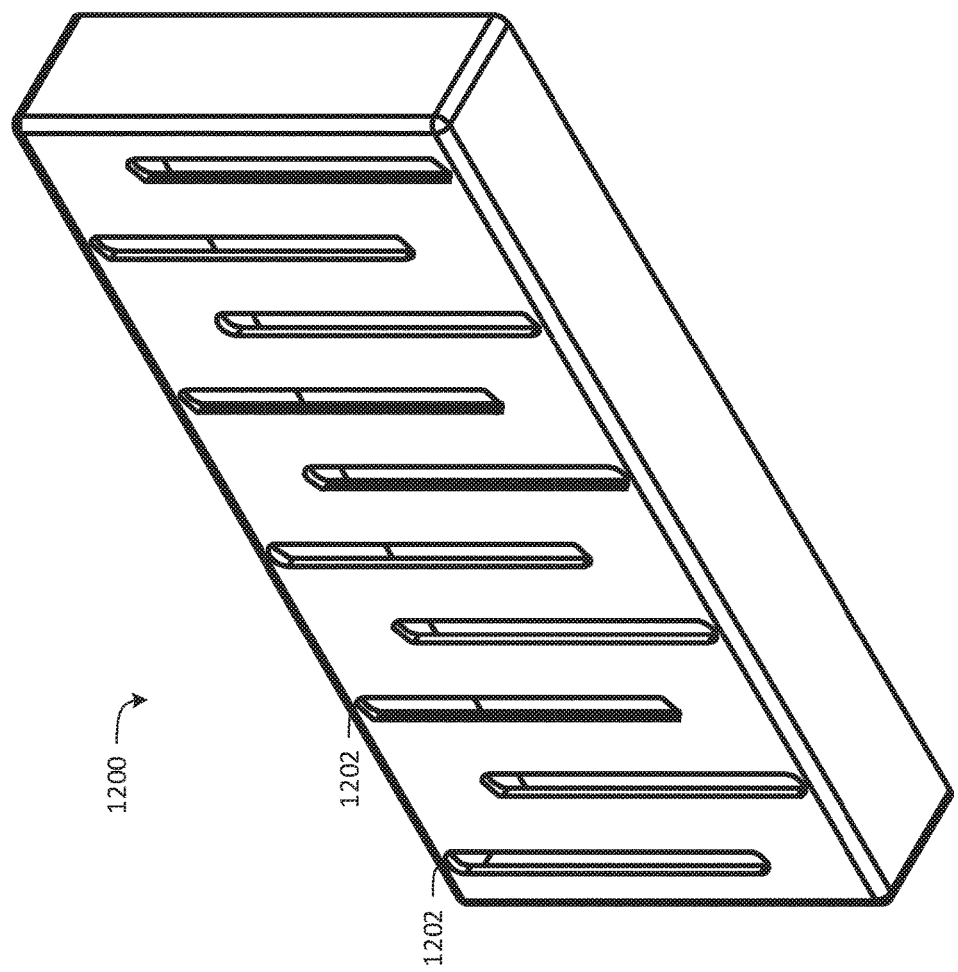
FIG. 12 is an offset frontal view of a container for managing sharps used with the system and method of the present invention.

An example of one possible container system 1200 is depicted in FIG. 12, although any suitable container system designed to contain sharps as established in the medical arts may be utilized. Container system 1200 organizes and contains suture packages in clear view for use during surgical procedures. Container system 1200 further includes one or more slots 1202 that are shaped and designated to hold various sharps such as needles, blades, sutures, etc. Thus, container system 1200 helps facilitate an accurate count of both used and unused needles at all times, which further decreases potential confusion of suture counting during a surgical procedure.

The disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

We claim:

1. A system for organizing a plurality of surgical instruments and a plurality of surgical supplies in a sterile operating room in preparation for a procedure, operation or surgery, the system comprising:
    a first tray for holding at least one medical instrument having a handle end and a working end, the first tray comprising:
        at least one substantially flat work surface disposed in a first reference plane;
        an edge feature surrounding the at least one substantially flat work surface, the edge feature having a top surface standing proud at a predetermined first positive offset distance from the first reference plane, the edge feature comprising at least a work-surface-side wall intersecting the at least one substantially flat work surface at an angle, wherein the top surface disposes generally parallel to the first reference plane and is further defining the first positive offset distance from the reference plane;
        at least one recessed compartment comprising a bottom surface disposed substantially parallel to the first reference plane and offset therefrom at a first negative offset distance to accommodate medical instruments;
    a second tray;
    a swing-arm bracket configured to engage the work surface of the first tray,
    the swing arm bracket comprising:
        a coupling member configured to engage a portion of the work-surface-side wall and work surface of the first tray, the coupling member further including a sleeve;
        a first arm member comprising a pin disposed on a proximal end, the pin configured to slidably engage the sleeve and whereby the pin rotates in the sleeve, the first arm member further comprising a distal end having a first-hinge end;
        a second arm member comprising a cooperating second-hinge end configured to hingeably engage the first-hinge end and disposed on a proximal end of the second aunt member, a distal end of the second arm member includes a post;
        the second tray comprises a post-receiving hole configured to rotatably receive the post of the second arm member, the second tray configured to be supported by the second arm member in at least one position offset from the tray;
        the second tray further comprises at least one work surface defining a reference plane, at least one recessed compartment offset at a negative distance from the reference plane configured to selectively hold at least one surgical instrument in a position whereby the working end is below the given reference plane.

2. A system for organizing a plurality of surgical instruments and a plurality of surgical supplies in a sterile operating room in preparation for a procedure, operation or surgery, the system comprising:
    a first tray for holding at least one medical instrument having a handle end and a working end, the first tray comprising:
        at least one substantially flat work surface disposed in a first reference plane;
        an edge feature surrounding the at least one substantially flat work surface, the edge feature having a top surface standing proud at a predetermined first positive offset distance from the first reference plane, the edge feature comprising at least a work-surface-side wall intersecting the at least one substantially flat work surface at an angle, wherein the top surface disposes generally parallel to the first reference plane and is further defining the first positive offset distance from the reference plane;

at least one recessed compartment comprising a bottom surface disposed substantially parallel to the first reference plane and offset therefrom at a first negative offset distance to accommodate medical instruments;

a second tray;

a linking support member adapted to couple to the first tray at a first proximal end of the linking support member and selectively attach to the second tray at a second distal end of the linking support member whereby the linking support member is further configured to enable the second tray to rotate into and out of a field of sterilization and further configured to rotatably move from a first position over the first tray; and the linking support member further comprising an intermediate hinge disposed between the distal and proximal ends; and at least one surgical drape having at least one predefined area printed thereon, the surgical drape configured to cover a back table in the operating room, the predefined area indicating the systematic placement of at least one surgical instrument or supply.

3. A system for organizing a plurality of surgical instruments and a plurality of surgical supplies in a sterile operating room in preparation for a procedure, operation or surgery, the system comprising:

a first tray for holding at least one medical instrument having a handle end and a working sharps-end, the first tray comprising:
at least one substantially flat work surface disposed in a first reference plane;
an edge feature surrounding the at least one substantially flat work surface, the edge feature having a top surface standing proud at a predetermined first positive offset distance from the first reference plane, the edge feature comprising at least a work-surface-side wall intersecting the at least one substantially flat work surface at an angle, wherein the top surface disposes generally parallel to the first reference plane and is further defining the first positive offset distance from the reference plane;
at least one recessed compartment comprising a bottom surface disposed substantially parallel to the first reference plane and offset therefrom at a first negative offset distance from the reference plane to accommodate medical instruments;

a first support truss disposed substantially intermediate to the reference plane and the bottom surface, the first support truss comprising at least one tool-support notch and a cooperating and corresponding second support truss comprising at least one support groove disposed at a negative offset distance from the reference plane;

a second tray;

a linking support member adapted to couple to the first tray at a first proximal end of the linking support member and selectively attach to the second tray at a second distal end of the linking support member whereby the linking support member is further configured to enable the second tray to rotate into and out of a field of sterilization; and the linking support member further comprising a hinge disposed between the distal and proximal ends.

4. The system of claim 3, wherein the second support truss further comprises:
the support groove being disposed at a negative offset from the reference plane and the support groove further configured whereby the instrument inserted in the cooperating tool-support notch and support groove arranges the working sharps-end of the medical instrument to lie below the first reference plane.

5. A system for organizing a plurality of surgical instruments and a plurality of surgical supplies in a sterile operating room in preparation for a procedure, operation or surgery, the system comprising:

a first tray for holding at least one medical instrument having a handle end and a working sharps-end, the first tray comprising:
at least one substantially flat work surface disposed in a first reference plane;
an edge feature surrounding the at least one substantially flat work surface, the edge feature having a top surface standing proud at a predetermined first positive offset distance from the first reference plane, the edge feature comprising at least a work-surface-side wall intersecting the at least one substantially flat work surface at an angle, wherein the top surface disposes generally parallel to the first reference plane and is further defining the first positive offset distance from the reference plane;
at least one recessed compartment comprising a bottom surface disposed substantially parallel to the first reference plane and offset therefrom at a first negative offset distance from the reference plane to accommodate medical instruments;

a first support truss disposed substantially intermediate to the reference plane and the bottom surface, the first support truss comprising at least one tool-support notch and a cooperating and corresponding second support truss comprising at least one support groove disposed at a second negative offset distance from the reference plane;

a second tray;

a coupling member adapted to couple to the first tray at a first proximal end of the linking support member and selectively attach to the second tray at a second distal end of the linking support member whereby the linking support member is further configured to enable the second tray to rotate into and out of a field of sterilization and further configured to rotatably move from a first position over the first tray, the coupling member further including a sleeve; a first arm member comprising a pin disposed on a proximal end, the pin configured to slidably engage the sleeve and whereby the pin rotates in the sleeve, the first arm member further comprising a distal end having a first-hinge end; a second arm member comprising a cooperating second-hinge end configured to hingeably engage the first-hinge end and disposed on a proximal end of the second arm member.

6. The system of claim 5, wherein the second support truss further comprises:
the support groove being disposed at a second negative offset from the reference plane and the support groove further configured whereby the instrument inserted in the cooperating tool-support notch and support groove arranges the working sharps-end of the medical instrument to lie below the first reference plane.

* * * * *